US008163932B2

(12) United States Patent
Jones et al.

(10) Patent No.: US 8,163,932 B2
(45) Date of Patent: *Apr. 24, 2012

(54) SUBSTITUTED INDOLEALKANOIC ACIDS

(75) Inventors: Michael Lee Jones, Chapel Hill, NC (US); David Gunn, Hamden, CT (US); John Howard Jones, Framingham, MA (US); Michael C. Van Zandt, Guilford, CT (US)

(73) Assignee: Alinea Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/701,967

(22) Filed: Feb. 8, 2010

(65) Prior Publication Data

US 2010/0137301 A1 Jun. 3, 2010

Related U.S. Application Data

(60) Division of application No. 11/999,524, filed on Dec. 4, 2007, now Pat. No. 7,659,269, which is a continuation of application No. 11/531,151, filed on Sep. 12, 2006, now Pat. No. 7,304,079, which is a continuation of application No. 10/832,724, filed on Apr. 27, 2004, now Pat. No. 7,105,514, which is a continuation of application No. 10/185,863, filed on Jun. 28, 2002, now Pat. No. 6,730,794, which is a continuation of application No. 09/818,808, filed on Mar. 27, 2001, now Pat. No. 6,426,344, which is a continuation of application No. 09/282,280, filed on Mar. 31, 1999, now Pat. No. 6,214,991.

(60) Provisional application No. 60/080,143, filed on Mar. 31, 1998.

(51) Int. Cl.
*C07D 417/06* (2006.01)
*C07D 209/04* (2006.01)
*A61K 31/535* (2006.01)
*A61K 31/425* (2006.01)
*A61K 31/40* (2006.01)

(52) U.S. Cl. ..... 548/159; 548/491; 544/135; 514/235.2; 514/367; 514/419

(58) Field of Classification Search ................ None
See application file for complete search history.

(56) References Cited

U.S. PATENT DOCUMENTS

| 3,557,142 | A | 1/1971 | Bell |
| 4,251,528 | A | 2/1981 | Brittain et al. |
| 4,283,539 | A | 8/1981 | Schnur |
| 4,438,126 | A | 3/1984 | Ueda et al. |
| 4,442,118 | A | 4/1984 | Dvornik et al. |
| 4,868,301 | A | 9/1989 | Mylari et al. |
| 4,939,140 | A | 7/1990 | Larson et al. |
| 4,960,785 | A | 10/1990 | Howard et al. |
| 5,064,852 | A | 11/1991 | Howard et al. |
| 5,116,753 | A | 5/1992 | Beattie et al. |
| 5,236,945 | A | 8/1993 | Mylari et al. |
| 5,304,557 | A | 4/1994 | Mylari |
| 5,312,829 | A | 5/1994 | Okada et al. |
| 5,330,997 | A | 7/1994 | Mylari et al. |
| 5,332,755 | A | 7/1994 | Butler et al. |
| 5,391,551 | A | 2/1995 | Peterson |
| 5,641,800 | A | 6/1997 | Bach et al. |
| 5,700,819 | A | 12/1997 | Aotsuka et al. |
| 5,744,488 | A | 4/1998 | Cross et al. |
| 6,214,991 | B1 | 4/2001 | Jones et al. |
| 6,426,344 | B2 | 7/2002 | Jones et al. |
| 6,521,659 | B2 * | 2/2003 | Sredy et al. .......... 514/415 |
| 6,730,794 | B2 | 5/2004 | Jones et al. |
| 6,964,980 | B2 | 11/2005 | Sredy et al. |
| 7,105,514 | B2 | 9/2006 | Jones et al. |
| 7,304,079 | B2 | 12/2007 | Jones et al. |
| 2002/0161025 | A1 | 10/2002 | Lebaut et al. |

FOREIGN PATENT DOCUMENTS

| EP | 0 054 417 A1 | 6/1982 |
| EP | 0 199 543 A2 | 10/1986 |
| EP | 0 222 576 | 5/1987 |
| EP | 0 401 981 A1 | 12/1990 |
| EP | 0427860 | 5/1991 |
| EP | 0458207 | 11/1991 |
| EP | 0 539 117 A1 | 4/1993 |
| EP | 0 624 369 A | 11/1994 |
| EP | 0 705 607 A | 4/1996 |
| EP | 714 893 A1 | 6/1996 |
| FR | 2 647 676 | 12/1990 |
| JP | 0641071 A * | 2/1994 |
| JP | 09 165371 | 6/1997 |
| WO | 93/12786 A1 | 7/1993 |
| WO | 95/06046 | 3/1995 |

(Continued)

OTHER PUBLICATIONS

Cross et al., "Selective Thromboxane Synthetase Inhibitors. 2. 3-(1H-Imidazol-1-ylmethyl)-2-methyl-1H-indole-1-propanoic Acid and Analogues", American Chemical Society, (1986), pp. 342-346.
Doebel et al., "Derivatives of Indole-1-acetic Acid as Antiinflammatory Agents", Journal of Medicinal Chemistry, (1972), vol. 15, No. 10, pp. 1081-1082.
Kador et al., "Aldose Reductase Inhibitors: A Potential New Class of Agents for the Harmacological Control of Certain Diabetic Complications", Journal of Medicinal Chemistry (American Chemical Society), (1985), vol. 28, No. 7, pp. 841-849.
Kador et al., "Pharmacophor Requirements of the Aldose Reductase Inhibitor Site", Molecular Pharmacology, (1983), vol. 24, pp. 521-531.
Aotsuka et al., "Benzothiazol-2-Ylcarboxylic Acids with Diverse Spacers: A Novel Class of Potent, Orally Active Aldose Reductase Inhibitors", Biorganic & Medicinal Chemistry Letters, (1997), vol. 7, No. 13, pp. 1677-1682.

(Continued)

*Primary Examiner* — Kamal Saeed
*Assistant Examiner* — Nyeemah A Grazier
(74) *Attorney, Agent, or Firm* — McDonnell Boehnen Hulbert & Berghoff LLP

(57) ABSTRACT

Disclosed are substituted indolealkanoic acids useful in the treatment of chronic complications arising from diabetes mellitus. Also disclosed are pharmaceutical compositions containing the compounds and methods of treatment employing the compounds, as well as methods for their synthesis.

17 Claims, No Drawings

FOREIGN PATENT DOCUMENTS

| WO | 95/31453 | 11/1995 |
|----|----------|---------|
| WO | 96/03376 A1 | 2/1996 |
| WO | 96/26207 | 8/1996 |
| WO | 99/50268 | 10/1999 |

OTHER PUBLICATIONS

Humber, Ph.D., L., "The Medicinal Chemistry of Aldose Reductase Inhibitors, Chapter 5", Aldose Reductase Inhibition (Biomedical Information Corporation), (1987), pp. 326-353.

Larson et al., "Medicinal Chemistry of Aldose Reductase Inhibitors", Medicinal Research Reviews, (1988), vol. 8, No. 2, pp. 159-186.

Dvornik D., "Inhibitors of Aldo Reductase, Chapter 16", Design of Enzyme Inhibitors as Drugs, (1994), vol. 2, pp. 710-738.

Matassa et al., "Evolution of a Series of Peptidoleukotriene Antagonists: Synthesis and Structure/Activity Relationships of 1,3,5-Substituted Indoles and Indazoles", J. Med. Chem., (1990), vol. 33, pp. 1781-1790.

Mylar et al., "Novel, Potent Aldose Reductase Inhibitors: 3,4-Dihydro-4-oxo-3-[[5-(trifluoromethyl)-2-benzothiazolyl]methyl]-1-phthalazine-acetic Acid (Zopolrestat) and Congeners", J. Med. Chem., (1991), vol. 34, No. 1, pp. 108-122.

Aotsuka et al., "Novel and Potent Aldose Reductase Inhibitors: 4-Benzyl- and 4-(Benzothiazol-2-ylmethyl)-3,4-dihydro-3-oxo-2H-1,4-benzothiazine-2-acetic Acid Derivatives", Chem. Pharm. Bull., (1994), vol. 42, No. 6, pp. 1264-1271.

Dickinson, Roger P. et al., "Thromboxane Modulating Agents. 2. Thromboxane Receptor Antagonists Derived from teh Thromboxane Synthase Inhibitor Dazmegrel", Bioorganic & medicinal Chemistry Letters, vol. 6, No. 14, pp. 1691-1696.

Whitehead, Calvert W., "Effect of Lipophilic Substituents on Some Biological Properties of Indoles", Journal of Medicinal Chemistry, 1974, vol. 17, No. 12, pp. 1298-1304.

Patini, et al., "Bioisosterism: a rational approach in drug design" Chem Rev., 1996, vol. 96(8), pp. 3147-3176.

\* cited by examiner

SUBSTITUTED INDOLEALKANOIC ACIDS

This is a continuation-in-part of application Ser. No. 60/080,143, filed Mar. 31, 1998.

BACKGROUND OF INVENTION

The use of aldose reductase inhibitors (ARIs) for the treatment of diabetic complications is well known. The complications arise from elevated levels of glucose in tissues such as the nerve, kidney, retina and lens that enters the polyol pathway and is converted to sorbitol via aldose reductase. Because sorbitol does not easily cross cell membranes, it accumulates inside certain cells resulting in changes in osmotic pressure, alterations in the redox state of pyridine nucleotides (i.e. increased $NADH/NAD^+$ ratio) and depleted intracellular levels of myoinositol. These biochemical changes, which have been linked to diabetic complications, can be controlled by inhibitors of aldose reductase.

The use of aldose reductase inhibitors for the treatment of diabetic complications has been extensively reviewed, see: (a) *Textbook of Diabetes*, 2nd ed.; Pickup, J. C. and Williams, G. (Eds.); Blackwell Science, Boston, Mass. 1997.; (b) Larson, E. R.; Lipinski, C. A. and Sarges, R., *Medicinal Research Reviews*, 1988, 8 (2), 159-198; (c) Dvornik, D. *Aldose Reductase Inhibition*. Porte, D. (ed), Biomedical Information Corp., New York, N.Y. Mc Graw Hill 1987; (d) Petrash, J. M., Tarle, I., Wilson, D. K. Quiocho. F. A. Perspectives in Diabetes, *Aldose Reductase Catalysis and Crystalography: Insights From Recent Advances in Enzyme Structure and Function*, Diabetes, 1994, 43, 955; (e) Aotsuka, T.; Abe, N.; Fukushima, K.; Ashizawa, N. and Yoshida, M., *Bioorg. & Med. Chem. Letters*, 1997, 7, 1677, (f), T., Nagaki, Y.; Ishii, A.; Konishi, Y.; Yago, H; Seishi, S.; Okukado, N.; Okamoto, K., *J. Med. Chem.*, 1997, 40, 684; (g) Ashizawa, N.; Yoshida, M.; Sugiyama, Y.; Akaike, N.; Ohbayashi, S.; Aotsuka, T.; Abe, N.; Fukushima, K.; Matsuura, A, *Jpn. J. Pharmacol.* 1997, 73, 133; (h) Kador, P. F.; Sharpless, N. E., *Molecular Pharmacology*, 1983, 24, 521; (I) Kador, P. F.; Kinoshita, J. H.; Sharpless, N. E., *J. Med. Chem.* 1985, 28 (7), 841; (j) Hotta, N., *Biomed. & Pharmacother.* 1995, 5, 232; (k) Mylar, B.; Larson, E. R.; Beyer, T. A.; Zembrowski, W. J.; Aldinger, C. E.; Dee, F. D.; Siegel, T. W.; Singleton, D. H., *J. Med. Chem.* 1991, 34, 108; (l) Dvornik, D. *Croatica Chemica Acta* 1996, 69 (2), 613.

Previously described aldose reductase inhibitors most closely related to the present invention include those sighted in: (a) U.S. Pat. No. 5,700,819: 2-Substituted benzothiazole derivatives useful in the treatment of diabetic complications, (b) U.S. Pat. No. 4,868,301: Processes and intermediates for the preparation of oxophthalazinyl acetic acids having benzothiazole or other heterocyclic side chains, (c) U.S. Pat. No. 5,330,997: 1H-indazole-3-acetic acids as aldose reductase inhibitors, and (d) U.S. Pat. No. 5,236,945: 1H-indazole-3-acetic acids as aldose reductase inhibitors. Although many aldose reductase inhibitors have been extensively developed, none have demonstrated sufficient efficacy in human clinical trials without significant undesirable side effects. Thus no aldose reductase inhibitors are currently available as approved therapeutic agents in the United States; and consequently, there is still a significant need for new, efficacious and safe medications for the treatment of diabetic complications.

SUMMARY OF THE INVENTION

This invention provides compounds that interact with and inhibit aldose reductase. Thus, in a broad aspect, the invention provides compounds of Formula I:

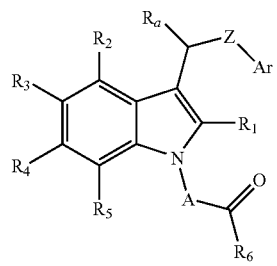

or pharmaceutically acceptable salts thereof wherein
A is a $C_1$-$C_4$ alkylene group optionally substituted with $C_1$-$C_2$ alkyl or mono- or disubstituted with halogen, preferably fluoro or chloro;
Z is a bond, O, S, C(O)NH, or $C_1$-$C_3$ alkylene optionally substituted with $C_1$-$C_2$ alkyl;
$R_1$ is hydrogen, alkyl having 1-6 carbon atoms, halogen, 2-, 3-, or 4-pyridyl, or phenyl, where the phenyl or pyridyl is optionally substituted with up to three groups selected from halogen, hydroxy, $C_1$-$C_6$ alkoxy, $C_1$-$C_6$ alkyl, nitro, amino, or mono- or di($C_1$-$C_6$)alkylamino;
$R_2$, $R_3$, $R_4$ and $R_5$ are each independently
hydrogen, halogen, nitro, or an alkyl group of 1-6 carbon atoms (which may be substituted with one or more halogens);
$OR_7$, $SR_7$, $S(O)R_7$, $S(O)_2$ $(R_7)_2$, $C(O)N(R_7)_2$, or $N(R_7)_2$, wherein each $R_7$ is independently hydrogen, an alkyl group of 1-6 carbon atoms (which may be substituted with one or more halogens) or benzyl, where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino; phenyl or heteroaryl such as 2-, 3- or 4-imidazolyl or 2-, 3-, or 4-pyridyl, each of which phenyl or heteroaryl is optionally substituted with up to three groups independently selected from halogen, $C_1$-$C_6$ alkyl, $C_1$-$C_6$ alkoxy, amino, and mono- or di($C_1$-$C_6$)alkylamino;
phenoxy where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino; or
a group of the formula

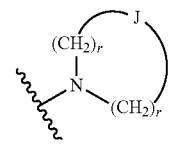

where
J is a bond, $CH_2$, oxygen, or nitrogen; and
each r is independently 2 or 3;
$R_6$ is hydroxy or a prodrug group;
$R_a$ is hydrogen, $C_1$-$C_6$ alkyl, fluoro, or trifluoromethyl; and
Ar represents aryl or heteroaryl, each of which is optionally substituted with up to five groups.

In another aspect, the invention provides methods for preparing such compounds.

The compounds of the invention inhibit aldose reductase. Since aldose reductase is critical to the production of high levels of sorbitol in individuals with diabetes, inhibitors of aldose reductase are useful in preventing and/or treating various complications associated with diabetes. The compounds of the invention are therefore effective for the treatment of diabetic complications as a result of their ability to inhibit aldose reductase.

Thus, in another aspect, the invention provides methods for treating and/or preventing chronic complications associated with diabetes mellitus, including, for example, diabetic cataracts, retinopathy, nephropathy, and neuropathy.

In still another aspect, the invention provides pharmaceutical compositions containing compounds of Formula I.

DETAILED DESCRIPTION OF THE INVENTION

The numbering system for the compounds of Formula I is as follows:

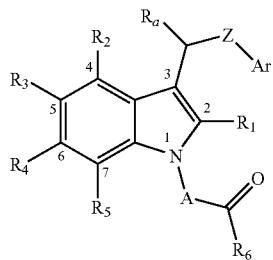

I

As noted above, the invention provides novel substituted indole alkanoic acids useful in treating and/or preventing complications associated with or arising from elevated levels of glucose in individuals suffering from diabetes mellitus. These compounds are represented by Formula I above.

In compounds of Formula I, the aryl and heteroaryl groups represented by Ar include:

a phenyl group optionally substituted with up to 5 groups independently selected from halogen, an alkyl group of 1-6 carbon atoms (which may be substituted with one or more halogens), nitro, $OR_7$, $SR_7$, $S(O)R_7$, $S(O)_2R_7$ or $N(R_7)_2$ wherein $R_7$ is hydrogen, an alkyl group of 1-6 carbon atoms (which may be substituted with one or more halogens) or benzyl, where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino, or the phenyl group may be condensed with benzo where the benzo is optionally substituted with one or two of halogen, cyano, nitro, trifluoromethyl, perfluoroethyl, trifluoroacetyl, or ($C_1$-$C_6$)alkanoyl, hydroxy, ($C_1$-$C_6$)alkyl, ($C_1$-$C_6$)alkoxy. ($C_1$-$C_6$)alkylthio, trifluoromethoxy, trifluoromethylthio, ($C_1$-$C_6$)alkylsulfinyl, ($C_1$-$C_6$)alkylsulfonyl;

a heterocyclic 5-membered ring having one nitrogen, oxygen or sulfur, two nitrogens one of which may be replaced by oxygen or sulfur, or three nitrogens one of which may be replaced by oxygen or sulfur, said heterocyclic 5-membered ring substituted by one or two fluoro, chloro, ($C_1$-$C_6$)alkyl or phenyl, or condensed with benzo, or substituted by one of pyridyl, furyl or thienyl, said phenyl or benzo optionally substituted by one of iodo, cyano, nitro, perfluoroethyl, trifluoroacetyl, or ($C_1$-$C_6$)alkanoyl, one or two of fluoro, chloro, bromo, hydroxy, ($C_1$-$C_6$)alkyl, ($C_1$-$C_6$) alkoxy, ($C_1$-$C_6$)alkylthio, trifluoromethoxy, trifluoromethylthio, ($C_1$-$C_6$)alkylsulfinyl, ($C_1$-$C_6$)alkylsulfonyl or trifluoromethyl, or two fluoro or two trifluoromethyl with one hydroxy or one ($C_1$-$C_6$)alkoxy, or one or, preferably, two fluoro and one trifluoromethyl, or three fluoro, said pyridyl, furyl or thienyl optionally substituted in the 3-position by fluoro, chloro, bromo, ($C_1$-$C_6$)alkyl or ($C_1$-$C_6$)alkoxy;

a heterocyclic 6-membered ring having one to three nitrogen atoms, or one or two nitrogen atoms and one oxygen or sulfur, said heterocyclic 6-membered ring substituted by one or two ($C_1$-$C_6$)alkyl or phenyl, or condensed with benzo, or substituted by one of pyridyl, furyl or thienyl, said phenyl or benzo optionally substituted by one of iodo or trifluoromethylthio, or one or two of fluoro, chloro, bromo, ($C_1$-$C_6$)alkyl, ($C_1$-$C_6$)alkoxy, ($C_1$-$C_6$)alkylthio, ($C_1$-$C_6$)alkylsulfinyl, ($C_1$-$C_6$)alkylsulfonyl, or trifluoromethyl, and said pyridyl, furyl or thienyl optionally substituted in the 3-position by fluoro, chloro, ($C_1$-$C_6$)alkyl or ($C_1$-$C_6$)alkoxy;

said benzo-condensed heterocyclic 5-membered or 6-membered rings optionally substituted in the heterocyclic 5-membered or 6-membered ring by one of fluoro, chloro, bromo, methoxy, or trifluoromethyl;

oxazole or thiazole condensed with a 6-membered aromatic group containing one or two nitrogen atoms, with thiophene or with furane, each optionally substituted on by one of fluoro, chloro, bromo, trifluoromethyl, methylthio or methylsulfinyl;

imidazolopyridine or triazolopyridine optionally substituted by one of trifluoromethyl, trifluoromethylthio, bromo, or ($C_1$-$C_6$)alkoxy, or two of fluoro or chloro;

thienothiophene or thienofuran optionally substituted by one of fluoro, chloro or trifluoromethyl; thienotriazole optionally substituted by one of chloro or trifluoromethyl; naphthothiazole; naphthoxazole; or thienoisothiazole.

More specific compounds of the invention are those of Formula I wherein Ar is optionally substituted benzothiazolyl, benzoxazolyl, isoquinolyl, benzothiophen-yl, benzofuran-yl or benzimidazolyl, or substituted oxadiazolyl or indolyl. Other more specific compounds are of Formula I those wherein $R_a$ is trifluoromethyl, Z is a covalent bond or $CH_2$, $R_6$ is hydroxy, and each of $R_2$-$R_5$ are independently hydrogen, halogen, more preferably bromo or chloro, $C_1$-$C_2$ alkyl, phenoxy, benzyloxy, or $C_1$-$C_2$ alkoxy, and $R_1$ is hydrogen or methyl.

Preferred compounds of the invention are those wherein Z is a covalent bond, $R_6$ is hydroxy, Ar is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, benzothiophen-2-yl, benzofuran-2-yl, or thazolo[4,5-pyridine-2-y, thieno[2,3-b]pyridine2-yl, imidazo[1,5-a]pyridine-2-yl, or indol-2-yl, or substituted 1,2,4-oxadiazol-3-yl, 1,2,4-oxadiazol-5-yl, isothiazol-5-yl, isothiazol-4-yl, 1,2,5-thiadiazol-3-yl, oxazol-2-yl, thiazol-2-yl, or thiazol-4-yl, $R_2$-$R_5$ are independently hydrogen, halogen, more preferably bromo or chloro, $C_1$-$C_2$ alkyl, phenoxy, benzyloxy or phenyl where each phenyl portion is optionally substituted with $C_1$-$C_6$ alkyl, halogen, $C_1$-$C_6$ alkoxy, hydroxy, amino or mono- or di ($C_1$-$C_6$) alkylamino $R_a$ is hydrogen, fluoro or $C_1$-$C_2$ alkyl, and $R_1$ is hydrogen or methyl.

Other preferred compounds are those wherein the methylene bridge connecting the indolyl group with Ar is located alpha with respect to a nitrogen atom in Ar, e.g. wherein Ar is benzoxazol-2-yl or 1,2,4-oxadiazol-3-yl mentioned above.

Other more specific compounds of the invention are those wherein Z is a covalent bond, $R_6$ is hydroxy, $R_a$ is hydrogen, Ar is optionally 4,5,6 or 7 benzo-substituted benzothiazolyl, benzoxazolyl, benzimidazolyl, benzothiophenyl, benzofuranyl, or indolyl, or Ar is 2-benzothiazolyl substituted on benzo by one trifluoroacetyl or trifluoromethylthio, or one or two of fluoro chloro, bromo, hydroxy, methyl, methoxy, trifluoromethyl, trifluoromethoxy, trifluoromethylthio, or one or, preferably, two fluoro and one trifluoromethyl, or two fluoro or two trifluoromethyl with one methoxy, or three fluoro, or by 6,7-benzo, and those wherein one of $R_2$ and $R_3$ is hydrogen, fluoro, chloro, bromo or methyl, and one of $R_4$ and $R_5$ is hydrogen, or chloro, bromo, methyl, isopropyl, methoxy, nitro or trifluoromethyl; or $R_3$ and $R_4$ are 5,6-difluoro, $R_a$ is hydrogen; and those wherein Ar is optionally substituted benzothiazol-2-yl or quinoxalyl and $R_3$ and $R_4$ are each chloro, and $R_1$ is hydrogen or methyl.

Further more specific compounds are those wherein Z is a covalent bond, $R_6$ is hydroxy, Ar is optionally substituted benzothiazol-2-yl, $R_3$ and $R_4$ are hydrogen, and $R_5$ is methyl; those wherein Z is a covalent bond, $R_6$ is hydroxy, $R_3$, $R_4$ and $R_5$ are hydrogen, chloro, fluoro, bromo or $C_1$-$C_2$ alkyl, $R_a$ is hydrogen, and Ar is optionally 4,5,6 or 7 benzosubstituted benzothiazolyl-2-trifluoromethyl, benzoxazolyl-2-trifluoromethyl, benzimidazolyl-2-trifluoromethyl, benzofuran-2-trifluoromethyl, benzofuran-3-trifluoromethyl, benzothiophen-2-trifluoromethyl, benzothiophen-3-trifluoromethyl, indolyl-2-trifluoromethyl, or indolyl-3-trifluoromethyl; and those wherein Z is $CH_2$, $R_6$ is hydroxy, Ar is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, or thiazolo[4,5-b]pyridine-2-yl, or substituted 1,2,4-oxadiazol3-yl, 1,2,4-oxadiazol-5-yl, isothiazol-5-yl, isothiazol-4-yl, 1,3,4-oxadiazol-5-yl, 1,2,5-thiadiazol-3-yl, oxazol-2-yl, thiazol-2-yl, or thiazol-4-yl, and $R_3$, $R_4$ and $R_5$ are independently hydrogen, chloro, fluoro, bromo, $C_1$-$C_2$ alkyl, or trifluoromethyl, and $R_a$ is hydrogen.

Generally, $R_1$ in the specific compounds described above is hydrogen, halogen, preferably chloro or fluoro, $C_1$-$C_6$ alkyl, or phenyl optionally substituted with up to three groups independently selected from halogen, $C_1$-$C_6$ alkyl, $C_1$-$C_6$ alkoxy, amino, and mono- or di($C_1$-$C_6$)alkylamino. Preferred $R_1$ groups are hydrogen and methyl.

Preferred compounds of the invention include those where Ar in Formula I is substituted phenyl, i.e., compounds of Formula II:

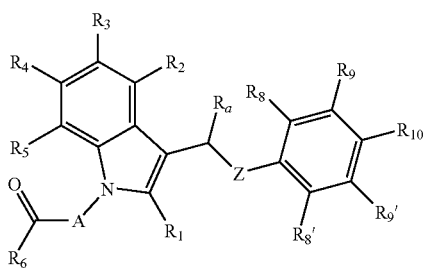

II wherein
A is a $C_1$-$C_4$ alkylene group optionally substituted with $C_1$-$C_2$ alkyl;
Z is a bond, or $C_1$-$C_3$ alkylene optionally substituted with $C_1$-$C_2$ alkyl;
$R_a$ is hydrogen, $C_1$-$C_6$ alkyl, chloro, bromo, fluoro, or trifluoromethyl;

$R_1$ is hydrogen, $C_1$-$C_6$ alkyl, fluoro, or phenyl optionally substituted with up to three groups independently selected from halogen, $C_1$-$C_6$ alkyl, $C_1$-$C_6$ alkoxy, amino, and mono- or di($C_1$-$C_6$)alkylamino;

$R_2$, $R_3$, $R_4$ and $R_5$ are each independently hydrogen, halogen, an alkyl group of 1-6 carbon atoms (which may be substituted with one or more halogens), nitro, $OR_7$, $SR_7$, $S(O)R_7$, $S(O)_2N(R_7)_2$, $C(O)N(R_7)_2$, or $N(R_7)_2$, wherein each $R_7$ is independently hydrogen, an alkyl group of 1-6 carbon atoms (which may be substituted with one or more halogens) or benzyl, where the phenyl portion is optionally substituted with up to three groups independently selected from halogen, $C_1$-$C_6$ alkyl, $C_1$-$C_6$ alkoxy, amino, and mono- or di($C_1$-$C_6$) alkylamino;

phenyl or heteroaryl such as 2-, 3- or 4-imidazolyl or 2-, 3, or 4-pyridyl, each of which phenyl or heteroaryl is optionally substituted with up to three groups independently selected from halogen, $C_1$-$C_6$ alkyl, $C_1$-$C_6$ alkoxy, amino, and mono- or di($C_1$-$C_6$)alkylamino;

phenoxy where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino; or a group of the formula

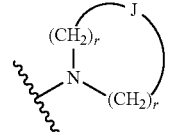

where

J is a bond, $CH_2$, oxygen, or nitrogen; and each r is independently 2, or 3;

$R_6$ is hydrogen, an alkoxy group of 1-6 carbon atoms, or —$O^-M^+$ where $M^+$ is a cation forming a pharmaceutically acceptable salt; and $R_8$, $R_9$, and $R_{10}$ are independently hydrogen, fluorine, chlorine, bromine, trifluoromethyl or nitro.

Other preferred compounds of the invention are those where Ar is a substituted benzothiazole, i.e., compounds of Formula III:

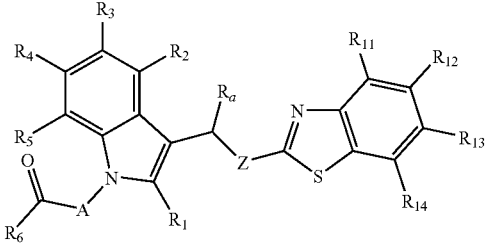

III wherein

A is a $C_1$-$C_4$ alkylene group optionally substituted with $C_1$-$C_2$ alkyl;

Z is a bond, or $C_1$-$C_3$ alkylene optionally substituted with $C_1$-$C_2$ alkyl;

$R_a$ is hydrogen, $C_1$-$C_6$ alkyl, chloro, bromo, fluoro, or trifluoromethyl;

$R_1$ is hydrogen, $C_1$-$C_6$ alkyl, halogen, preferably chloro or fluoro, or phenyl optionally substituted with up to three groups independently selected from halogen, $C_1$-$C_6$ alkyl, $C_1$-$C_6$ alkoxy, amino, and mono- or di($C_1$-$C_6$)alkylamino;

$R_2$, $R_3$, $R_4$ and $R_5$ are each independently hydrogen, halogen, an alkyl group of 1-6 carbon atoms (which may be substituted with one or more halogens), nitro, $OR_7$, $SR_7$, $S(O)R_7$, $S(O)_2N(R_7)_2$ $C(O)N(R_7)_2$ or $N(R_7)_2$, wherein each $R_7$ is independently hydrogen, an alkyl group of 1-6 carbon atoms (which may be substituted with one or more halogens) or benzyl, where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino;

phenyl or heteroaryl such as 2-, 3- or 4-imidazolyl or 2-, 3-, or 4-pyridyl, each of which phenyl or heteroaryl is optionally substituted with up to three groups independently selected from halogen, $C_1$-$C_6$ alkyl, $C_1$-$C_6$ alkoxy, amino, and mono- or di($C_1$-$C_6$)alkylamino;

phenoxy where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino; or a group of the formula

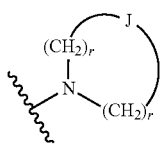

where
J is a bond, $CH_2$, oxygen, or nitrogen; and
each r is independently 2 or 3;

$R_6$ is hydroxy, $C_1$-$C_6$ alkoxy, or $-O^-M^+$ where $M^+$ is a cation forming a pharmaceutically acceptable salt; and $R_{11}$, $R_{12}$, $R_{13}$ and $R_{14}$ are independently hydrogen, halogen, nitro, hydroxy, $C_1$-$C_6$ alkyl, $C_1$-$C_6$ alkoxy, $C_1$-$C_6$ alkylthio, trifluoromethyl, trifluoromethoxy, $C_1$-$C_6$ alkylsulfinyl, or $C_1$-$C_6$ alkylsulfonyl.

In preferred compounds of Formula III, the $R_2$, $R_3$, $R_4$ and $R_5$ substituents, in combination, represent one of bromo, cyano or nitro, one or two of fluoro, chloro, hydroxy, ($C_1$-$C_6$) alkyl, ($C_1$-$C_6$)alkoxy, or trifluoromethyl, or two fluoro or two methyl with one hydroxy or one ($C_1$-$C_6$)alkoxy, or one or, preferably, two fluoro and one methyl, or three fluoro groups. Particularly preferred $R_2$, $R_3$, $R_4$ and $R_5$ substituents are, independently, fluorine, chlorine, nitro, and trifluoromethyl.

In preferred compounds of Formulas II and III, A is preferably methylene, methylene substituted with a methyl group, or ethylene.

Preferred compounds according to Formula II above include those wherein $R_8$ is fluorine, $R_9$ is hydrogen and $R_{10}$ is bromine or those wherein $R_8$ and $R_{10}$ are hydrogens and $R_9$ is nitro.

Preferred compounds of Formula III above are those wherein the benzothiazole moiety is substituted with nitro, one, two, or three of fluoro, one or two of chloro, or at least one trifluoromethyl group. More preferred compounds of Formula II are those where A is methylene, $R_1$ is hydrogen or methyl, Z is a bond, and $R_6$ is hydroxy or $C_1$-$C_6$ alkoxy.

Still more preferred compounds of Formula II are those wherein $R_{11}$, $R_{12}$ and $R_{14}$ are fluorines and $R_{13}$ is hydrogen. Other more preferred compounds of Formula II are those where $R_a$ is methyl or hydrogen, Z is methylene or, more preferably, a bond, A is CHF or $C_1$ or $C_2$ alkylene, preferably methylene, $R_1$ is methyl or hydrogen, and $R_{11}$, $R_{12}$ and $R_{14}$ are halogens or $C_1$-$C_3$ alkyl. Still other more preferred compounds of Formula III are those where $R_a$ is methyl or hydrogen, Z is methylene or, more preferably, a bond, A is CHF or $C_1$ or $C_2$ alkylene, $R_1$ is methyl or hydrogen, and $R_{11}$, $R_{12}$ and $R_{14}$ are fluorines or chlorines.

Particularly preferred compounds of Formula I are those where $R_3$ and $R_4$ are independently hydrogen, $C_1$-$C_6$ alkyl, $C_1$-$C_6$ alkoxy, or halogen, and $R_a$ is methyl or hydrogen, Z is a bond, A is methylene, methyl substituted methylene, or ethylene, $R_1$ is methyl or hydrogen, and $R_{11}$, $R_{12}$ and $R_{14}$ are fluorines or chlorines.

The term "prodrug group" denotes a moiety that is converted in vivo into the active compound of formula I wherein $R_6$ is hydroxy. Such groups are generally known in the art and include ester forming groups, to form an ester prodrug, such as benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$)alkoxy optionally substituted by N-morpholino and amide-forming groups such as di($C_1$-$C_6$)alkylamino. Preferred prodrug groups include hydroxy, $C_1$-$C_6$ alkoxy, and $O^-M^+$ where $M^+$ represents a cation. Preferred cations include sodium, potassium, and ammonium. Other cations include magnesium and calcium. Further preferred prodrug groups include $O^-M^{++}$ where $M^{++}$ is a divalent cation such as magnesium or calcium.

In certain situations, compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention include the pharmaceutically acceptable acid addition salts of compounds where $R_6$ includes basic nitrogen atom, i.e, an alkylamino or morpholino group. In addition, if the compound or prodrug of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-ACOOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used herein, the terms 2-benzothiazolyl and benzothiazol-2-yl are synonymous.

Representative groups of the formula

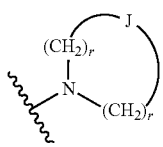

include those where J is oxygen and each r is 2 (morpholinyl), J is nitrogen and each r is 2 (piperazinyl) or one r is 2 and the other 3 (homopiperazinyl), or J is CH$_2$ and each r is 2 (piperidinyl) or one r is 2 and the other 3 (homopiperidinyl). Preferred groups of this formula are morpholinyl and piperazinyl.

The heterocyclic 5-membered ring having one to three nitrogen atoms, one of which may be replaced by oxygen or sulfur includes imidazolyl, oxazolyl, triazolyl, pyrazolyl, oxadiazolyl, thiadiazolyl, and triazolyl.

The heterocyclic 6-membered ring having one to three nitrogen atoms, or one or two nitrogen atoms and one oxygen or sulfur includes triazinyl, pyrimidyl, pyridazinyl, oxazinyl and triazinyl.

The heterocyclic ring may be condensed with benzo so that said ring is attached at two neighboring carbon atoms to form a phenyl group. Such benzoheterocyclic ring may be attached to Z either through the heterocyclic group or through the benzo group of the benzoheterocyclic ring. Specific wherein said heterocyclic ring is condensed with a benzo include benzoxazolyl, quinazolin-2-yl, 2-benzimidazolyl, quinazolin-4-yl and benzothiazolyl. The oxazole or thiazole condensed with a 6-membered aromatic group containing one or two nitrogen atoms include positional isomers such as oxazolo[4,5-b]pyridine-2-yl, thiazolo[4,5-b]pyridine-2-yl, oxazolo[4,5-c]pyridine-2-yl, thiazolo[4,5-c]pyridine-2-yl, oxazolo[5,4-b]pyridine-2-yl, thiazolo[5,4-b]pyridine-2-yl, oxazolo[5,4-c]pyridine-2-yl, and thiazolo[5,4-c]pyridine-2-yl.

The following compounds of the invention are provided to give the reader an understanding of the compounds encompassed by the invention:
3-(4,5,7-trifluorobenzothiazol-2-yl) methyl-indole-N-acetic acid
5-chloro-3-(4,5,7-trifluorobenzothiazol-2-yl)methyl-indole-N-acetic acid
2-methyl-3-(4,5,7-trifluorobenzothiazol-2-yl)methyl-indole-N-acetic acid
5-methyl-3-(4,5,7-trifluorobenzothiazol-2-yl)methyl-indole-N-acetic acid
7-methyl-3-(4,5,7-trifluorobenzothiazol-2-yl)methyl-indole-N-acetic acid
6-chloro-3-(4,5,7-trifluorobenzothiazol-2-yl)methyl-indole-N-acetic acid
5-benzyloxy-3-(4,5,7-trifluorobenzothiazol-2-yl)methyl-indole-N-acetic acid
6-fluoro-3-(4,5,7-trifluorobenzothiazol-2-yl)methyl-indole-N-acetic acid
5-fluoro-3-(4,5,7-trifluorobenzothiazol-2-yl)methyl-indole-N-acetic acid
6-methyl-3-(4,5,7-trifluorobenzothiazol-2-yl)methyl-indole-N-acetic acid
3-methyl(4,5,7-trifluorobenzothiazol-2-yl)methyl-indole-N-2 propionic acid
3-methyl(4,5,7-trifluorobenzothiazol-2-yl)methyl-indole-N-3 propionic acid
3-(5-trifluoromethylbenzothiazol-2-yl)methyl-indole-N-acetic acid
5-methyl-3-(5-trifluoromethylbenzothiazol-2-yl)methyl-indole-N-acetic acid
3-(3-nitrophenyl)methyl-indole-N-acetic Acid The above compounds, further described in the Examples and other description of the invention below, are illustrative but are not meant to limit in any way the scope of the contemplated compounds according to the present invention.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels on the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 1000 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The compounds of the present invention may be prepared by use of known chemical reactions and procedures. General methods for synthesizing the compounds are presented below. It is understood that the nature of the substituents required for the desired target compound often determines the preferred method of synthesis. All variable groups of these methods are as described in the generic description if they are not specifically defined below. More detailed procedures for particular examples are presented below in the experimental section.

Methods of Preparation

The compounds of the invention where Ar is benzothiazolyl can be conveniently prepared from a substituted indole moiety using general Scheme A set forth below.

Scheme A

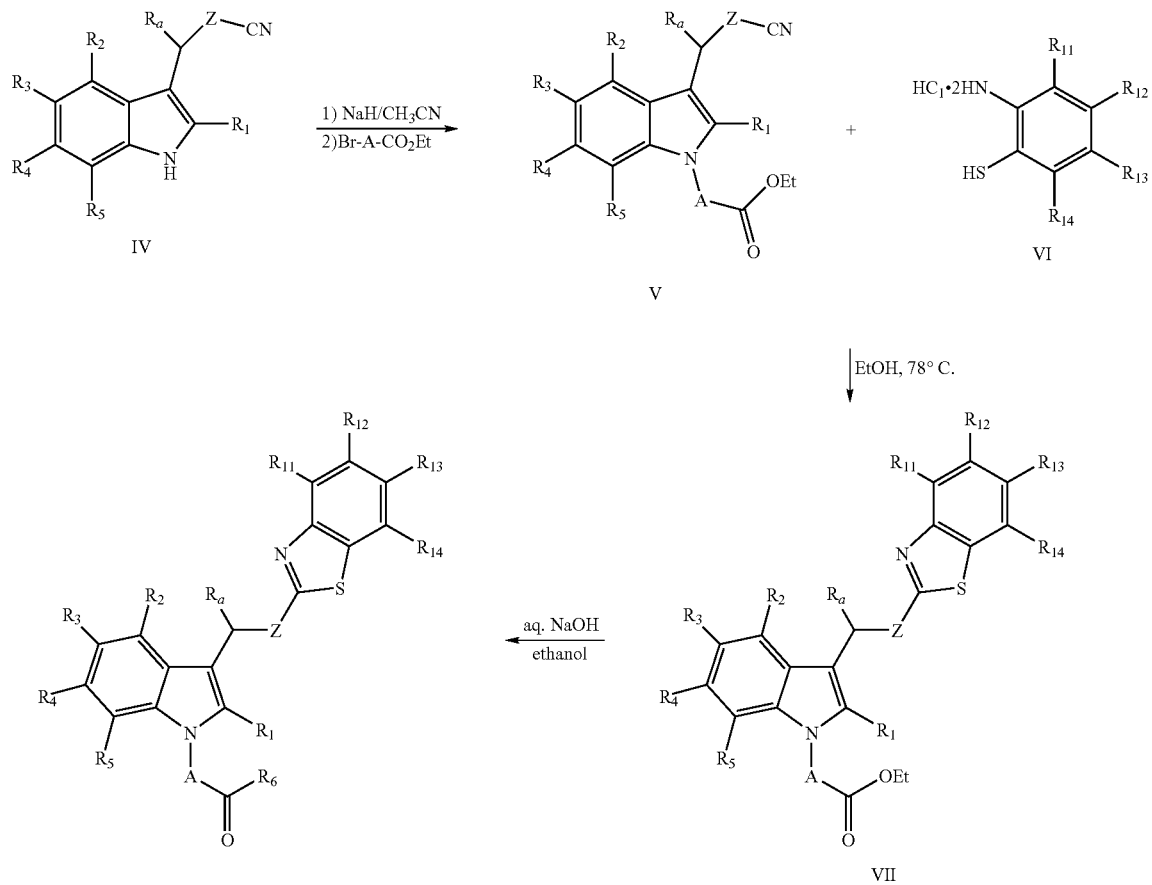

Tent of a nitrile indole IV with a strong base such as, for example, sodium hydride, butyl lithium or sodium tert-butoxide, in a polar aprotic solvent such as acetonitrile, tetrahydrofuran or N,N-dimethylformamide followed by an treatment with an alkylating agent, e.g., ethyl or tert-butyl bromoacetate, provides the desired N-alkylated product V. Alternatively, phase transfer catalysis can be used in a biphasic solvent system. A general review of such alkylations can be found in Sundberg, R. J. *Indoles*; Chapter 11, Academic Press Inc., San Diego, Calif., 1996. Condensation with a suitable 2-amino thiophenol hydrochloride salt VI provides benzothiazole intermediate VII. These reactions are most often carried out in an alcohol solvents at elevated temperatures; however, other solvents like N,N-dimethylformamide and N-methylpyrrolidone can be used or the reactions can be carried out in the absence of solvents altogether. The scope of the reaction conditions useful for this transformation have been described previously (U.S. Pat. No. 5,700,819). General methods for the preparation of various substituted 2-amino thiophenols are also well known (*J. Med. Chem.* 1991, 34, 108 and *Chem. Pharm. Bull.* 1994, 42, 1264). In general, the best method of synthesis is determined by such factors as availability of starting materials and ease of synthesis. Deprotection of the alkanoic acid moiety VII can be carried out by methods common to those skilled in the art to result in compounds of Formula III. The method used in the deprotection depends on the type of protecting group. A description of such protecting groups and methods for deprotecting them may be found in: *Protective Groups in Organic Synthesis*, Second Edition, T. W. Green and P. G. M. Wuts, John Wiley and Sons, New York, 1991. When a methyl or ethyl ester is used, an aqueous sodium hydroxide solution in ethanol or dimethoxyethane is conveniently employed for its removal.

If not commercially available, nitrile IV can be prepared substantially as described below in Scheme B depicting the formation of 3-acetonitrile substituted indoles of Formula IV where Z is a bond. Thus, an indole moiety in a weak acid solution, for example, acetic acid in ethanol, is treated with aqueous formaldehyde and dimethyl amine in an alcohol solvent. The 3-(dimethylamino)methyl indole product can then be treated with sodium or potassium cyanide in N,N-dimethylformamide at elevated temperatures to provide the 3-acetonitrile substituted indole intermediate. Alternatively, an iminium salt like N,N-dimethylmethyleneammonium chloride can be used to prepare the 3-(dimethylamino)methyl indole intermediate.

Scheme B

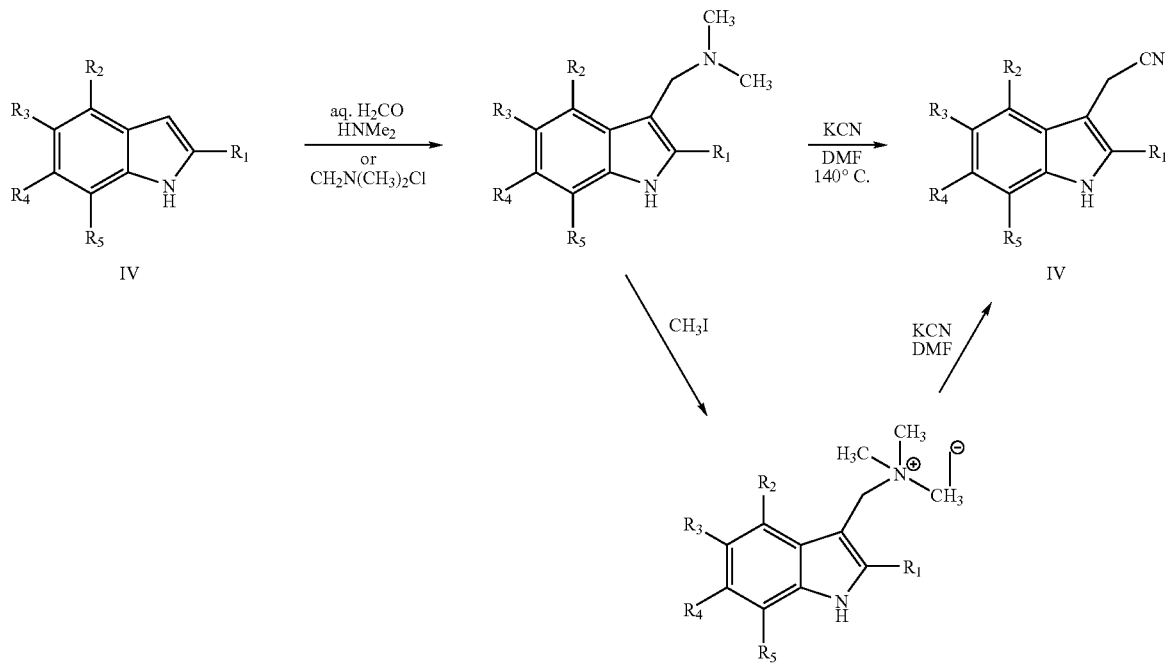

The 3-(dimethylamino)methyl indole intermediate can also be converted to the 3-acetonitrile substituted indole intermediate via the trimethyl ammonium salt. The salt can be prepared by treating the gramine intermediate with an alkalating agent like methyl iodide. The trimethyl ammonium salt intermediate can then be converted to the nitrile by treatment with sodium or potassium cyanide in a solvent like N,N-dimethylformamide. In general, the conversion to the acetonitrile occurs under more mild conditions when the trimethyl ammonium salt is used.

Alternatively, other compounds, such as those where Z—Ar represents a wide variety of substituted heterocycles, may be prepared using the general method outlined in Scheme C. Here, substituted indole intermediates where X is an activating group like hydroxyl, halogen, dialkyl amino, trialkyl ammonium or benzotriazole are coupled with Q-Z—Ar groups using methods well-established in indole chemistry. Examples of these methods where Q is Na or H and Z is sulfur, oxygen, nitrogen carbon or a bond are described in (A) Tidwell, J. H.; Peat, A. J.; Buchwald, S. L. *J. Org. Chem.* 1994, 59, 7164; (B) Bruneau, P.; Delvare, C.; Edwards, M. P.; McMillan, R. M. *J. Med. Chem.* 1991, 34, 1028; (C) Gan, T.; Cook, J. M. *Tetrahedron Lett.* 1997, 38, 1301; (D) Cerreto, F.; Villa, A.; Retico, A.; Scalzo, M. *Eur. J. Med. Chem.* 1992, 27 701; (E) Majchrzak, M. W.; Zobel, J. N.; Obradovich, D. J.; *Synth. Commun.* 1997, 27, 3201; (F) DeLeon, C. Y.; Ganem, B. *J. Org. Chem.* 1996, 61, 8730; (G) Katritzky, A. R.; Toader, D; Xie, L. *J. Org. Chem.* 1996, 61, 7571.

It is understood that, depending on the specific chemistry used, a protecting group, P, may be required. In general, P represents groups such as acyloxy, alkyl, sulfonyl or A-COOR. The use of these general methods is illustrated in *Protective Groups in Organic Synthesis*, Second Edition, T. W. Green and P. G. M. Wuts, John Wiley and Sons, New York, 1991.

Scheme C

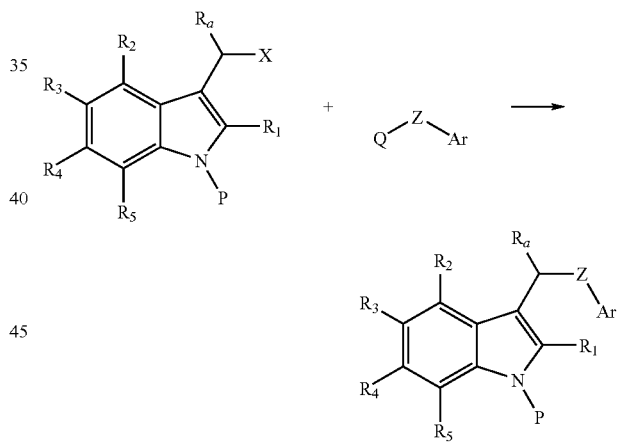

In general, the intermediate compounds wherein $R_{2-6}$ is aryl or heteroaryl can be synthesized by the chemistry illustrated in reaction Scheme D below. For example, treatment of the potassium salt of an optionally substituted bromoindole with tert-butyllithium at low temperature in an ethereal solvent such as ether or tetrahydrofuran followed by the addition of an electrophile represents a general method for obtaining substituted indoles, as described by Rapoport, H. (*J. Org. Chem.* 1986, 51, 5106). For a discussion of a synthesis where R is acyl, see *Biorg. Med. Chem. Lett.* 1999, 9, 333; where R is, thiomethyl, see *Heterocycles,* 1992, 34, 1169; and where R is cycloalkyl, see *J. Med. Chem.* 1999, 42, 526.

More specifically the addition of a trialkyl borate followed by an acidic work-up provides the desired indole boronic acids (*Heterocycles,* 1992, 34, 1169). Indole boronic acids can be used in well established transition metal catalyzed coupling reactions like the Suzuki reaction to provide aryl and heteroaryl indoles. These reactions are most often carried out in a mixture of ethereal or alcohol solvents with aqueous base in the presence of palladium catalyst, such as Pd(OAc)$_2$, Pd(OAc)$_2$ w/PPh$_3$ or Pd(PPh$_3$)$_4$ as described in *Tetrahedron Lett.* 1998, 39, 4467, *J. Org. Chem.* 1999, 64, 1372 and *Heterocycles* 1992, 34, 1395.

Alternatively, an optionally substituted bromoindole can be treated with an arylboronic acid and a palladium catalyst to provide arylindoles in large quantities (*Synlett* 1994, 93). A general review of Suzuki cross-couplings between boronic acids and aryl halides can be found in Miyaura, N; Suzuki, *A. Chem. Rev.* 1995, 95, 2457.

In addition, certain organometallic reactions eliminate the need for de novo construction of the indole nucleus. For example, the Stille reaction serves as a general method for the synthesis of regiocontrolled substitution of indole intermediates as described by Farina, V.; Krishnamurthy, V; Scott, W., *Organic Reactions,* 1998, 50, 1-652. As indicated in the scheme below, the indole may serve as the organotin species or the aryl halide. The stannylindole (XII), where P is a suitable protecting group such as [2-(trimethyl)ethoxy]methyl (SEM) or an alkyl substituent, is treated with a variety of partners (i.e., vinyl/allylic halides, vinyl triflates, aryl/heteroaryl halides and acyl halides) in the presence of a Pd(0)L$_n$ catalyst to provide the desired indoles (XII) (*Synnlett* 1993,

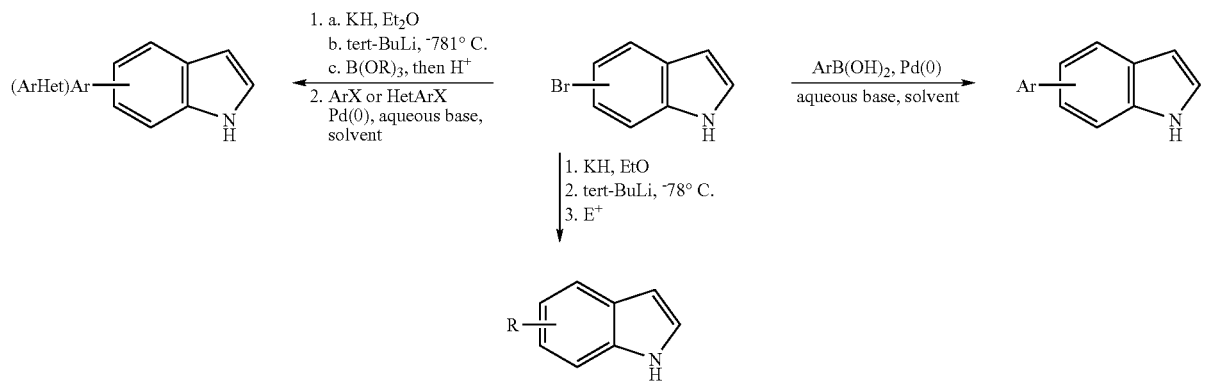

For example, treatment of the advanced intermediate indole X with an aryl or heteroaryl boronic acid using Pd-mediated coupling conditions provides the desired aryl and heteroaryl indole product XI as shown in scheme (E). In general the utility of this method is determined by the ease of synthesis of advanced intermediates of type X and the commercial availability of aryl and heteroaryl boronic acids.

771, *Helv. Chim. Acta* 1993, 76, 2356 and *J. Org. Chem.* 1994, 59, 4250). Conversely, a haloindole (XIV) is treated with a variety of tin reagents under Stille conditions to provide the desired substituted indoles (XV) as described in *Heterocycles* 1988, 27, 1585 and *Synth. Comm* 1992, 22, 1627).

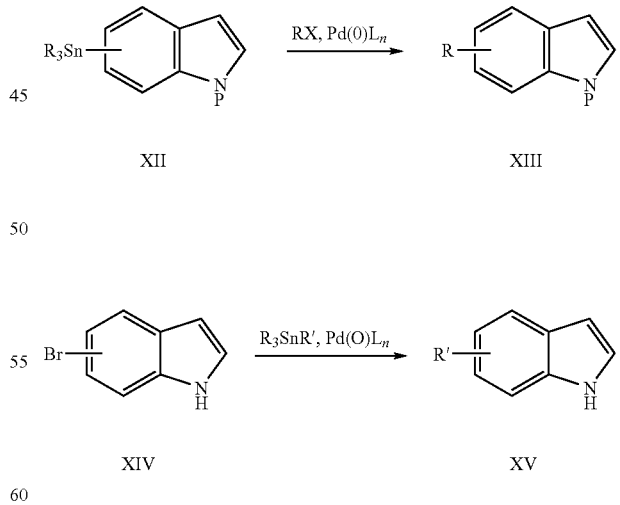

A general procedure for the synthesis of intermediate compounds using amines of the formula NR$_x$R$_{x2}$ (NR$_1$R$_2$ in the scheme below) is given in scheme F below. In Scheme F, R$_x$ and R$_{x2}$ are the same or different and represent hydrogen, C$_1$-C$_6$ alkyl, or R$_x$ and R$_{x2}$ together represent a group of the formula:

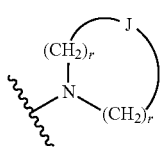

where J and each r is as defined above for formula I.

As shown in Scheme F, nucleophilic substitution of X (X is halogen, preferably fluorine) in an aromatic system is a method often used to substitute aromatic rings with amine and ether functionalities. Both 4- and 5-fluoro-2-nitrotoluene are sufficiently activated to undergo substitution with amines in the presence of $K_2CO_3$ in a polar aprotic solvent such as, for example, DMSO as described in *J. Med. Chem.* 1993, 36, 2716. The Leimgruber-Batcho two-step method is a general process for the construction of the indole ring system from the appropriate o-nitrotoluene. This reaction involves the condensation of an o-nitrotoluene with N,N-dimethylformamide dimethyl acetal followed by a reductive cyclization under suitable conditions such as hydrogen over a palladium catalyst or Zn/HOAc as described in Sundberg, R. J. *Indoles*; Chapter 2, Academic Press Inc., San Diego, Calif., 1996. A representative description of the process can also be found in *Organic Synthesis,* 1984, 63, 214.

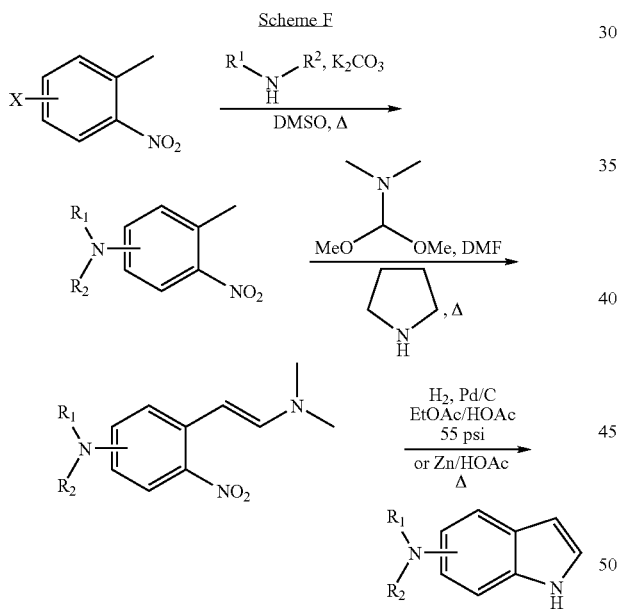

Scheme F

A general procedure for the synthesis of intermediate compounds wherein R is an aromatic, heteroaromatic or alkyl group is indicated in Scheme G below. As previously described, nucleophilic substitution of halogen, preferably fluorine, in an aromatic system is a method often used to substitute aromatic rings with amine and ether functionalities. Both 4- and 5-fluoro-2-nitrotoluene are sufficiently activated enough to undergo substitution with alcohols or phenols in the presence of $K_2CO_3$ in a polar aprotic solvent such as DMSO. A similar system using KOH and phenol is described in *J. Med. Chem.* 1994, 37, 1955. Alternatively, solid-liquid phase transfer catalysis (PTC) methods have been used to prepare intermediate ethers of this type as described in *Synth. Comm.* 1990, 20, 2855. The appropriately substituted o-nitrotoluene can then be converted to the appropriate indole by the Leimgruber-Batcho method previously described.

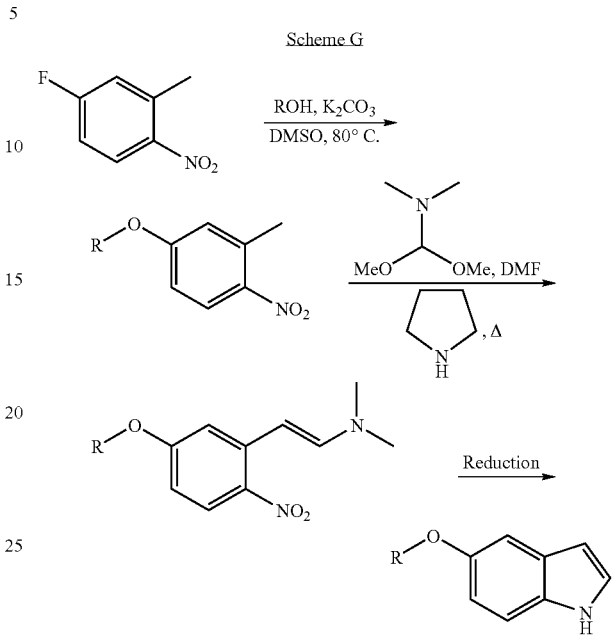

Scheme G

The preparation of intermediate alkoxy indole compounds wherein R is $C_2$-$C_6$ alkyl is outlined in Scheme H below. Commercially available nitrophenols can be alkylated under mild conditions with a base such as, for example, $K_2CO_3$ or $Cs_2CO_3$, in a polar aprotic solvent, e.g. $CH_3CN$, with a variety of suitable alkyl halides. See *Synth. Comm.* 1995, 25, 1367. The alkoxy o-nitrotoluene can then be converted to the desired indole as described above.

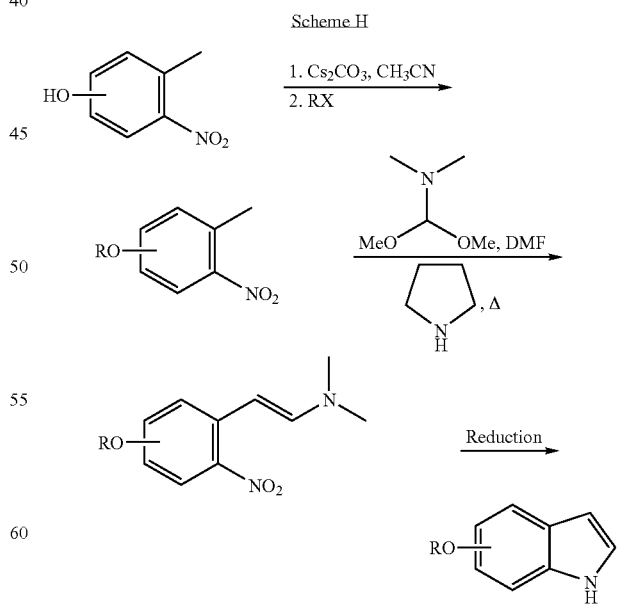

Scheme H

Alternatively, some examples of the invention where Z is a bond and Ar is a substituted heterocycle such as a thiazole; or Z is amide and Ar is a substituted phenyl can be conveniently prepared from an indole 3-acetic acid derivative as illustrated in Scheme I. Using this method, the carboxylic acid moiety is activated and coupled with an aryl amine. Some examples of activating methods well-known to those skilled in the art include formation of acid chloride, mixed anhydrides and coupling reagents such as 1,3-dicyclohexylcarbodiinide (DCC). A review of such method can be found in Bodanszky, M. *Principles of Peptide Synthesis*; Springer-Verlag: New York, 1984. For the examples where Z is a bond and Ar is a substituted benzothiazole or benzoxazole, the intermediate amide or thioamide can be cyclized into the aromatic ring. Examples of these types of heterocycle forming reactions are described in Mylar, B. L. et al. *J. Med. Chem.* 1991, 34, 108. In addition, the carboxylic acid can be converted to a chloro- or bromomethyl ketone and condensed with nucleophiles like thioamides or 2-aminothiophenols to produce thiazole or benzothiazine derivatives. Examples of methods to prepare the chloro- and bromomethyl ketones are illustrated in Rotella, D. P.; *Tetrahedron Lett.* 1995, 36, 5453 and Albeck, A.; Persky, R.; *Tetrahedron* 1994, 50, 6333. Depending on the reaction conditions in a given synthetic sequence a protecting group may be required. It is also understood that the specific order of steps used in the synthesis depends on the particular example being prepared. P may represent H, A-COOH, A-COO-lower alkyl or a simple protecting group that can be removed at a late stage of the synthesis. When such a protecting group is used, the A-CO2R6 group can be introduced near the end of the synthesis after the Z—Ar group has been assembled. Method of introducing the Z—Ar group are similar to those already described.

Scheme I

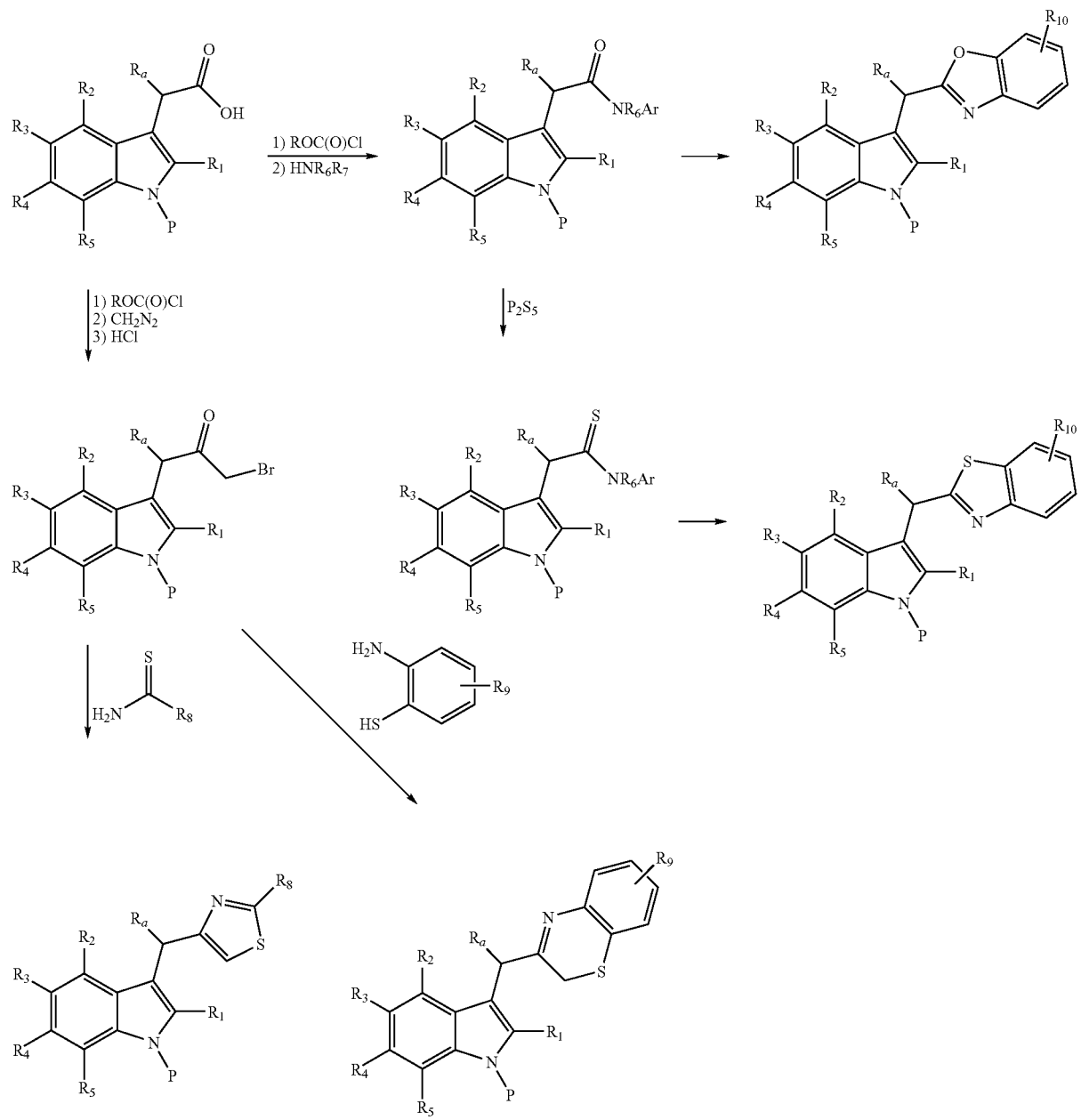

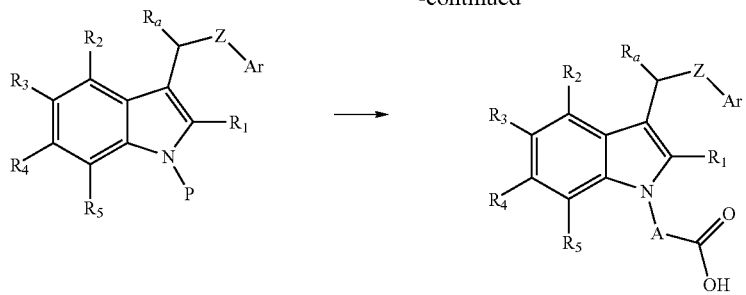

Another strategy involves the synthesis of substituted indoles via an intramolecular cyclization of an aniline nitrogen onto a substituted alkyne as shown in Scheme J. Typical approaches utilize commercially available o-iodoaniline derivatives. When these intermediates are unavailable, the regioselective ortho iodination of aromatic amines is used to generate the required intermediate (*J. Org. Chem.* 1996, 61, 5804). For example, Iodophenyl intermediates are treated with trimethylsilylacetylene in the presence of a Pd catalyst and a Cu(I) source, such as cupric iodide, to produce o-alkynylanilines. See *Heterocycles*, 1996, 43, 2471 and *J. Org. Chem.* 1997, 62, 6507. Further elaboration of the o-alkynylaniline to the desired indole can be done by a copper-mediated cyclization or a base-induced amine ring closure onto the alkyne functionality (*J. Med. Chem.* 1996, 39, 892). Alternative modifications have been made in the acetylenic derivatives to generate more elaborate indole structures as described in *J. Am. Chem. Soc.* 1991, 113, 6689, *Tetrahedron Lett.* 1993, 24, 2823 and *Tetrahedron Lett.* 1993, 34, 6471.

Scheme J

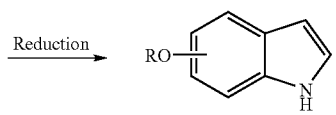

Those having skill in the art will recognize that the starting materials may be varied and additional steps employed to produce compounds encompassed by the present invention, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The disclosures in this application of all articles and references, including patents, are incorporated herein by reference.

The preparation of the compounds of the present invention is illustrated further by the following examples, which are not to be construed as limiting the invention in scope or spirit to the specific procedures and compounds described in them.

Example 1

Preparation of 2-methyl-3-(4,5,7-trifluorobenzothiazol-2-yl)methyl-indole-N-acetic acid

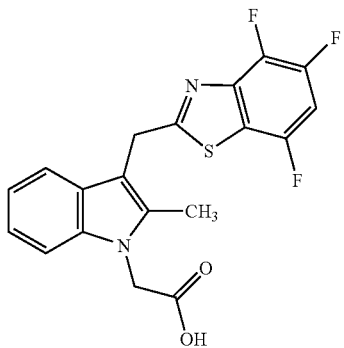

2-Methyl-3-(4,5,7-Trifluorobenzothiazol-2-yl)methyl-indole-N-acetic Acid was prepared in a manner analogous to that set forth in Example 2, except 2-methylindole was used instead of 5-chloroindole in step 1: 178-180° C.; $^1$H NMR (DMSO-d$_6$, 300 MHz) δ 7.75-7.62 (m, 1H), 7.45 (d, J=9.0 Hz, 1H), 7.39 (d, J=9.0 Hz, 1H), 7.08 (t, J=9 Hz, 1H), 6.99 (t, J=9.0 Hz, 1H), 5.00 (s, 2H), 4.60 (s, 2H), 2.38 (s, 3H); LRMS calcd for $C_{19}H_{13}F_3N_2O_2S$: 390.0. found 391.0 (M+1)$^+$. Anal. Calcd for $C_{19}H_{13}F_3N_2O_2S$: C, 58.46; H, 3.36; N, 7.18; S, 8.21. Found: C, 58.47; H, 3.29; N, 7.12; S, 8.18.

Example 2

Preparation of 5-chloro-3-(4,5,7-Trifluorobenzothiazol-2-yl)methyl-indole-N-acetic Acid

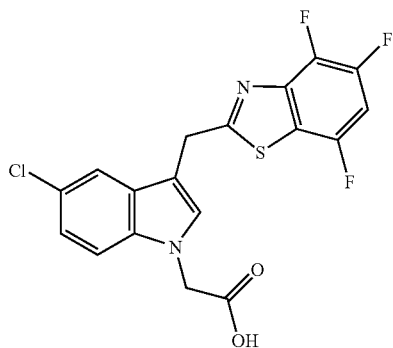

5-chloroindole-3-acetonitrile

A solution of aqueous formaldehyde (37%, 2.95 mL, 66.0 mmol) and dimethylamine (40%, 5.30 mL, 66.0 mmol) in 20 mL EtOH was cooled to 0° C. 5-Chloroindole (4.0 g, 26.4 mmol) was dissolved in a HOAc:EtOH mixture (1:1, 40 mL) and added dropwise to the reaction mixture. After stirring at this temperature for 2 h, the mixture was allowed to warm to room temperature and stir overnight. The mixture was added to a sat'd solution of NaHCO$_3$. 1 N NaOH was added until the pH was between 9-10. The resulting mixture was extracted with CH$_2$Cl$_2$ (3×). The organics were combined and washed with a sat'd aq. NaCl, dried over MgSO$_4$, filtered and concentrated in vacuo to give 4.65 g (85%) of 5-chloro-3-[(dimethylamino)methyl]indole as a yellow powder. Without further purification, 5-chloro-3-[(dimethylamino)methyl]indole (4.65 g, 22.4 mmol) was dissolved in dimethylformamide (80 mL) at room temperature with stirring. To this was added KCN (2.18 g, 33.5 mmol) in H$_2$O (10 mL). The mixture was warmed to 140° C. and stirred for 14 h. H$_2$O was added and the mixture was extracted with EtOAc (2×). The organics were combined and washed with sat'd brine, dried over MgSO$_4$, filtered and concentrated in vacuo. The residue was purified by SiO$_2$ flash chromatography (3:2, Heptane: EtOAc) to give 2.65 g (63%) of 5-chloroindole-3-acetonitrile. $^1$H NMR (DMSO-d$_6$, 300 MHz) δ 11.30 (br s, 1H), 7.63 (s, 1H), 7.42-7.38 (m, 2H), 7.05 (d, J=6.0 Hz, 1H), 5.70 (s, 2H),

5-chloro-3-(4,5,7-trifluorobenzothiazol-2-yl)methyl-indole-N-acetic acid 5-chloro-3-(4,5,7-trifluorobenzothiazol-2-yl)methyl-indole-N-acetic acid was prepared in a manner analogous to that set forth in Example 3 (steps 1-7), except 5-chloroindole-3-acetonitrile was used instead of 3-indolyl acetonitrile in step 5: mp 188-189° C.; $^1$H NMR (DMSO-d$_6$, 300 MHz) 7.73-7.68 (m, 1H), 7.63 (d, J=1.8 Hz, 1H), 7.51 (s, 1H), 7.45 (d, J=9.0 Hz, 1H), 7.14 (dd, J$_1$=9.0, J$_2$=2.4 Hz, 1H), 5.04 (s, 2H), 4.65 (s, 2H); LRMS calcd for C$_{18}$H$_{10}$F$_3$N$_2$O$_2$SCl: 410.0. found 411.0 (M+1)$^+$. Anal. Calcd for C$_{18}$H$_{10}$F$_3$N$_2$O$_2$SCl: C, 52.63; H, 2.45; N, 6.82; S, 7.81. Found: C, 52.56; H, 2.40; N, 6.71; S, 7.72.

Example 3

Preparation of 3-(4,5,7-Trifluorobenzothiazol-2-yl)methyl-indole-N-acetic Acid

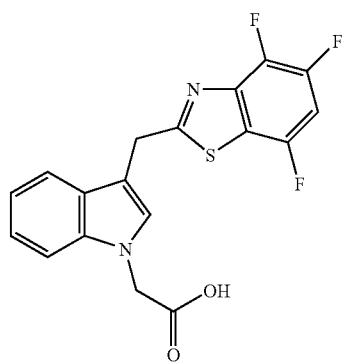

2,3,5,6-Tetrafluoroacetanilide

A solution of 2,3,5,6-tetrofluoroaniline (200 g, 1.21 mol) in anhydrous pyridine (103 mL, 1.27 mol) was treated with acetic anhydride (120 mL, 1.27 mol) and heated to 120° C. for 2 h. After cooling to room temperature, the solution was poured into ice-cold water (500 mL). The resulting precipitate was filtered, dissolved in ethyl acetate, dried over MgSO$_4$, filtered and concentrated. The solid material was washed with heptane (200 mL) and dried to give 2,3,5,6-tetrafluoroacetanilide as a white crystalline solid (206 g, 82%): mp 136-137° C.; R$_f$ 0.48 (50% ethyl acetate in heptane); $^1$H NMR (DMSO-d$_6$, 300 MHz) δ 10.10 (s, H), 7.87-7.74 (m, 1H), 2.09 (s, 3H). Anal. Calcd for C$_8$H$_5$F$_4$NO: C, 46.39; H, 2.43; N, 6.67. Found C, 46.35; H, 2.39; N, 6.68.

2,3,5,6-Tetrafluorothioacetanilide

A flame-dried, 4-necked 5,000 mL round-bottomed flask was charged with phosphorous pentasulfide (198 g, 0.45 mol) and diluted with anhydrous benzene (3,000 mL, 0.34 M). 2,3,5,6-tetrafluoroacetanilide (185 g, 0.89 mol) was added in one portion and the bright yellow suspension was heated to a gentle reflux for 3 h. The solution was cooled to 0° C. and filtered. The insoluble material was washed with ether (2×250 mL) and the combined filtrate was extracted with 10% aq. NaOH (750 mL, 500 mL). After cooling the aqueous layer to 0° C., it was carefully acidified with conc. HCl (pH 2-3). The precipitated product was collected by filtration and washed with water (500 mL). The yellow-orange material was dissolved in ethyl acetate (1,000 mL), dried over MgSO$_4$ and activated charcoal (3 g), filtered through a short pad of silica (50 g), and concentrated. The resulting solid was triturated with heptane (500 mL) and filtered to give 2,3,5,6-tetrafluorothioacetanilide (174.9 g, 88%): mp: 103-104° C.; R$_f$ 0.67 (50% ethyl acetate in heptane); $^1$H NMR (DMSO-d$_6$, 300 MHz) δ 11.20 (s, 1H), 8.00-7.88 (m, 1H), 2.66 (s, 3H). Anal. Calcd for C$_8$H$_5$F$_4$NS: C, 43.05; H, 2.26; N, 6.28. Found C, 43.10; H, 2.23; N, 6.19.

4,5,7-Trifluoro-2-methylbenzothiazole

A flame-dried 5,000 mL round-bottomed flask equipped with over-head stirrer was charged with sodium hydride (15.9 g, 0.66 mol) and diluted with anhydrous toluene (3,000 mL, 0.2 M). The suspension was cooled to 0° C., and treated with 2,3,5,6-tetrafluorothioacetanilide (134 g, 0.60 mol) in one portion. The solution was warmed to room temperature over 1 h, then heated to a gentle reflux. After 30 min, dimethylformamide (400 mL) was carefully added and the mixture was stirred for an additional 2 h. The solution was cooled to 0° C. and added to ice-water (2,000 mL). The solution was extracted with ethyl acetate (1,500 mL) and washed with sat'd. aq. NaCl (1,000 mL). The organic layer was concentrated to dryness, diluted with heptane and successively washed with water (300 mL) and sat'd. aq. NaCl (1,000 mL). The organic layer was dried over MgSO$_4$, filtered and concentrated to give 4,5,7-trifluoro-2-methylbenzothiazole (116.8 g, 96%) as a light brown solid: mp: 91-92° C.; R$_f$ 0.56 (30% ethyl acetate in heptane); $^1$H NMR (DMSO-d$_6$, 300 MHz) δ 7.76-7.67 (m, 1H), 2.87 (s, 3H). Anal. Calcd for C$_8$H$_4$F$_3$NS: C, 47.29; H, 1.98; N, 6.82; S, 15.78. Found C, 47.56; H, 2.07; N, 6.82; S, 15.59.

2-Amino-3,4,6-trifluorothiophenol Hydrochloride

A solution of 4,5,7-trifluoro-2-methylbenzothiazole (25.0 g, 123 mmol) in ethylene glycol (310 mL, 0.4 M) and 30% aq.

NaOH (310 mL, 0.4 M) was degassed using a nitrogen stream then heated to a gentle reflux (125° C.) for 3 h. The solution was cooled to 0° C. and acidified to pH 3-4 using conc. HCl (approx. 200 mL). The solution was extracted with ether (750 mL) and washed with water (200 mL). The organic layer was dried over $Na_2SO_4$, filtered and treated with 2,2-di-tert-butyl-4-methylphenol (0.135 g, 0.5 mol %). After concentrating to dryness, the crude product was dissolved in anhydrous methanol (200 mL) and treated with an HCl solution in 1,4-dioxane (37 mL, 4 N, 148 mmol). The resulting mixture was concentrated to dryness, triturated with isopropylether (100 mL) and filtered to give 2-amino-3,4,6-trifluorothiophenol hydrochloride (19.3 g, 73%) as a light brown solid that was used without further purification. mp. 121-124 C; $R_f$ 0.43 (30% ethyl acetate in heptane); Anal. Calcd for $C_6H_5ClF_3NS$: C, 33.42; H, 2.34; N, 6.50; S, 14.87. Found C, 33.45; H, 2.27; N, 6.48; S, 14.96.

3-cyanomethyl-indole-N-acetic acid, Ethyl Ester

Under an atmosphere of nitrogen, a solution of 3-indolyl acetonitrile (25.0 g, 160 mmol) in dry acetonitrile (530 mL, 0.3 M) was treated with sodium hydride (95%, 4.2 g, 168 mmol) and stirred for 30 min. Ethyl bromoacetate (21.3 mL, 192 mmol) was added in a dropwise manner over 10 min and the solution was stirred at room temperature for 16 h. After concentrating under reduced pressure, the resulting residue was dissolved in ethyl acetate and washed with sat'd. aq. NaCl. The organic extracts were dried over $MgSO_4$, filtered and concentrated. The crude product was recrystallized from heptane and ethyl acetate to give the target compound as a white crystalline solid (19 g, 49%): mp 98-99° C.; $R_f$ 0.29 (30% ethyl acetate in heptane); $^1$H NMR (DMSO-$d_6$, 300 MHz) δ 7.59 (dd, $J_1$=7.8 Hz, $J_2$=0.6 Hz, 1H), 7.40 (dd, $J_1$=8.1 Hz, $J_2$=0.6 Hz, 1H), 7.36 (s, 1H), 7.18 (b t, J=7.2 Hz, 1H), 7.10 (b t, J=7.2 Hz, 1H), 5.12 (s, 2H), 4.14 (q, J=7.2 Hz, 2H), 4.06, (s, 2H), 1.20 (t, J=7.2 Hz, 3H); LRMS calcd for $C_{14}H_{14}N_2O_2$: 242.3. found 243.0 (M+1)$^+$. Anal. Calcd for $C_{14}H_{14}N_2O_2$: C, 69.49; H, 5.82; N, 11.56. Found C, 69.39; H, 5.89; N, 11.59.

3-(4,5,7-trifluorobenzothiazol-2-yl)methyl-indole-N-acetic acid, Ethyl Ester Under a nitrogen atmosphere, a solution of 3-acetonitrile-indole-N-acetic acid, ethyl ester (11.0 g, 45.4 mmol) in anhydrous ethanol (90 mL, 0.5 M) was treated with 2-amino-3,4,6-trifluorothiophenol hydrochloride (12.7 g, 59.0 mmol) and heated to a gentle reflux for 16 h. After cooling to room temperature, the solution was concentrated under reduced pressure, diluted with ethyl acetate and washed with 2N HCl and sat'd. aq. NaCl. The organic layer was dried over $MgSO_4$, filtered and concentrated. Purification by MPLC (10-50% ethyl acetate in heptane, 23 mL/min, 150 min) to give 3-(4,5,7-trifluorobenzothiazol-2-yl)methyl-indole-N-acetic acid, ethyl ester (6.0 g, 36%) as a white crystalline solid: mp 110-111° C.; $R_f$ 0.41 (30% ethyl acetate in heptane); $^1$H NMR (DMSO-$d_6$, 300 MHz) δ 7.74-7.66 (m, 1H), 7.54 (d, J=7.8 Hz, 1H), 7.46 (s, 1H), 7.40 (d, J=8.1 Hz, 1H), 7.15 (br t, J=6.9 Hz, 1H), 7.04 (br t, J=7.8 Hz, 1H), 5.14, s, 2H), 4.66 (s, 2H), 4.14 (q, J=7.2 Hz, 3H); LRMS calcd for $C_{20}H_{15}F_3N_2O_2S$: 404.4. found 405.0 (M+1)$^+$. Anal. Calcd for $C_{20}H_{15}F_3N_2O_2S$; C, 59.40; H, 3.74; N, 6.93; S, 7.93. Found C, 59.52; H, 3.721; N, 6.92; S, 8.04.

3-(4,5,7-trifluorobenzothiazol-2-yl)methyl-indole-N-acetic acid

A solution of give 3-(4,5,7-trifluorobenzothiazol-2-yl)methyl-indole-N-acetic acid, ethyl ester (5.91 g, 14.6 mmol) in 1,2-dimethoxyethane (73 mL, 0.2 M) was cooled to 0° C. and treated with aq. NaOH (1.25 N, 58 mL, 73.1 mmol) in a dropwise manner over 15 min. After the addition was complete, the solution was stirred for an additional 30 min, acidified to pH 3 with 2N HCl, and concentrated under reduced pressure. The residue was dissolved in ethyl acetate (200 mL) and washed with sat'd. aq. NaCl (30 mL). The organic extract was dried over $Na_2SO_4$, filtered and concentrated. The resulting material was stirred as a suspension in heptane, filtered and dried to give 3-(4,5,7-trifluorobenzothiazol-2-yl)methyl-indole-N-acetic acid (5.38 g, 98%) as a pale yellow solid: mp 177-178° C.; $R_f$ 0.44 (20% methanol in dichloromethane); $^1$H NMR (DMSO-$d_6$, 300 MHz) δ 7.74-7.65 (m, 1H), 7.53 (d, J=7.5 Hz, 1H), 7.46 (s, 1H), 7.40 (d, J=8.1 Hz, 1H), 7.15 (b t, J=6.9 Hz, 1H), 7.03 (b t, J=7.2 Hz, 1H), 5.03 (s, 2H), 4.65 (s, 2H); LRMS calcd for $C_{18}H_{11}F_3N_2O_2S$: 376.4. found 375.0 (M−1)$^−$. Anal. Calcd for $C_{18}H_{11}F_3N_2O_2S$: C, 57.44; H, 2.95; N, 7.44; S, 8.52. Found C, 57.58; H, 2.99; N, 7.38; S, 8.51.

Example 4

Preparation of 5-methyl-3-(4,5,7-trifluorobenzothiazol-2-yl)methyl-indole-N-acetic acid

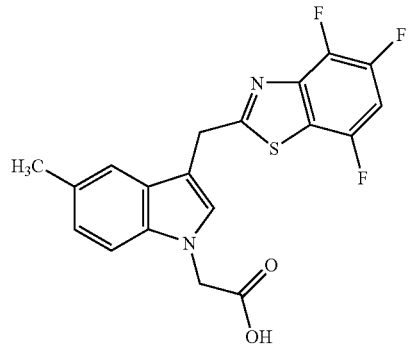

5-Methyl-3-(4,5,7-trifluorobenzothiazol-2-yl)methyl-indole-N-acetic Acid was prepared in a manner analogous to that set forth in Example 2, except 5-methylindole was used instead of 5-chloroindole in step 1: mp 131-133° C.; $^1$H NMR (DMSO-$d_6$, 300 MHz) δ 7.73-7.62 (m, 1H), 7.39 (s, 1H), 7.30 (s, 1H), 7.27 (d, J=9.0 Hz, 1H), 6.96 (dd, $J_1$=9.0 Hz, $J_2$=2.4 Hz, 1H), 4.98 (s, 2H), 4.60 (s, 2H), 2.32 (s, 3H); LRMS calcd for $C_{19}H_{13}F_3N_2O_2S$: 390.0. found 391.0 (M+1)$^+$. Anal. Calcd for $C_{19}H_{13}F_3N_2O_2S$: C, 58.46; H, 3.36; N, 7.18; S, 8.21. Found: C, 58.36; H, 3.30; N, 7.10; S, 8.20.

Example 5

Preparation of 7-methyl-3-(4,5,7-trifluorobenzothiazol-2-yl)methyl-indole-N-acetic acid 7-Methyl-3-(4,5,7-trifluorobenzothiazol-2-yl)methyl-indole-N-acetic Acid was prepared in a manner analogous to that set forth in Example 2, except 7-methylindole was used instead of 5-chloroindole in step 1: mp 216-218° C.; $^1$H NMR (DMSO-$d_6$, 300 MHz) δ 7.73-7.63 (m, 1H), 7.36-7.32 (m, 2H), 6.92-6.88 (m, 2H), 5.17 (s, 2H), 4.60 (s, 2H), 2.55 (s, 3H); LRMS calcd for $C_{19}H_{13}F_3N_2O_2S$: 390.0. found 391.0 (M+1)$^+$. Anal. Calcd for $C_{19}H_{13}F_3N_2O_2S$: C, 58.46; H, 3.36; N, 7.18; S, 8.21. Found: C, 58.37; H, 3.37; N, 7.11; S, 8.13.

Example 6

Preparation of 6-chloro-3-(4,5,7-trifluorobenzothiazol-2-yl)methyl-indole-N-acetic acid 6-Chloro-3-(4,5,7-trifluorobenzothiazol-2-yl)methyl-indole-N-acetic Acid was prepared in a manner analogous to that set forth in Example 2, except 6-chloroindole was used instead of 5-chloroindole in step 1: mp 194-195° C.; $^1$H NMR (DMSO-$d_6$, 300 MHz) δ 7.73-7.63 (m, 1H), 7.50 (d, J=8.4 Hz, 1H), 7.46-7.42 (m, 2H), 7.00 (dd, $J_1$=8.4 Hz, $J_2$=2.1 Hz, 1H), 4.76 (s, 2H), 4.62 (s, 2H); LRMS calcd for $C_{18}H_{10}F_3N_2O_2SCl$: 410.0. found 411.0 (M+1)$^+$. Analysis calculated for $C_{18}H_{10}F_3N_2O_2SCl$: C, 52.63; H, 2.45; N, 6.82; S, 7.81. Found: C, 52.50; H, 2.44; N, 6.74; S, 7.69.

Example 7

Preparation of 5-benzyloxy-3-(4,5,7-trifluorobenzothiazol-2-yl)methyl-indole-N-acetic acid

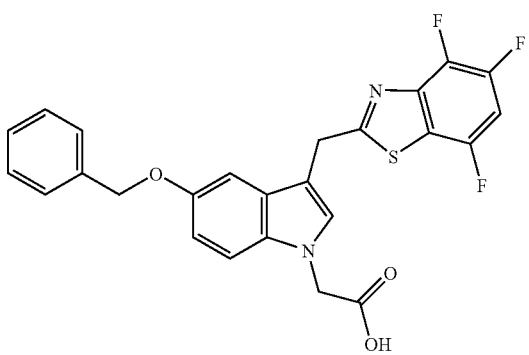

5-Benzyloxy-3-(4,5,7-trifluorobenzothiazol-2-yl)methyl-indole-N-acetic Acid was prepared in a manner analogous to that set forth in Example 2, except 5-benzyloxyindole was used instead of 5-chloroindole in step 1: mp 165-168° C.; $^1$H NMR (DMSO-$d_6$, 300 MHz) δ 7.73-7.65 (m, 1H) 7.40-7.30 (m, 3H), 7.28-7.10 (m, 4H), 7.10 (d, J=2.4 Hz, 1H), 6.87-6.80 (m, 1H), 5.05 (s, 2H), 4.95 (s, 2H), 4.57 (s 2H); LRMS calcd for $C_{25}H_{17}F_3N_2O_2S$: 482.0. found 483.0 (M+1)$^+$.

Example 8

Preparation of 6-fluoro-3-(4,5,7-trifluorobenzothiazol-2-yl)methyl-indole-N-acetic acid 6-fluoro-3-(4,5,7-trifluorobenzothiazol-2-yl)methyl-indole-N-acetic Acid was prepared in a manner analogous to that set forth in Example 2, except 6-fluoroindole was used instead of 5-chloroindole in step 1: mp 200-203° C.; $^1$H NMR (DMSO-$d_6$, 300 MHz) δ 7.73-7.65 (m, 1H), 7.53 (dd, $J_1$=8.4 Hz, $J_2$=3.3 Hz, 1H), 7.44 (s, 1H), 7.34 (dd, $J_1$=10.5 Hz, $J_2$=2.4 Hz, 1H), 6.93-6.68 (m, 1H), 5.11 (s, 2H), 4.64 (s, 2H); LRMS calcd for $C_{18}H_{10}F_4N_2O_2S$: 394.0. found 395 (M+1).

Example 9

Preparation of 5-fluoro-3-(4,5,7-trifluorobenzothiazol-2-yl)methyl-indole-N-acetic acid

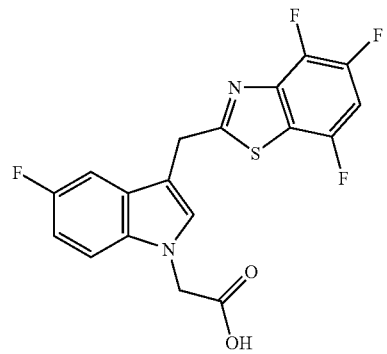

5-fluoro-3-(4,5,7-trifluorobenzothiazol-2-yl)methyl-indole-N-acetic Acid was prepared in a manner analogous to that set forth in Example 2, except 5-fluoroindole was used instead of 5-chloroindole in step 1: mp 193-195° C.; $^1$H NMR (DMSO-$d_6$, 300 MHz) δ 7.65 (m, 1H), 7.51 (s, 1H), 7.42 (br dd, $J_1$=9.0 Hz, $J_2$=4.8 Hz, 1H), 7.34 (br dd, $J_1$=9.9 Hz, $J_2$=2.4 Hz, 1H), 7.02-6.96 (m, 1H), 5.03 (s, 2H), 4.62 (s, 2H); LRMS calcd for $C_{18}H_{10}F_4N_2O_2S$: 394.0. found 395 (M+1).

Example 10

Preparation of 6-methyl-3-(4,5,7-trifluorobenzothiazol-2-yl)methyl-indole-N-acetic acid 6-methyl-3-(4,5,7-trifluorobenzothiazol-2-yl)methyl-indole-N-acetic Acid was prepared in a manner analogous to that set forth in Example 2, except 6-methylindole was used instead of 5-chloroindole in step 1: mp 211-213° C., $R_f$ 0.50 (10% methanol in dichloromethane); $^1$H NMR (DMSO-$d_6$, 300 MHz) 7.72-7.63 m, 1H), 7.37 (d, J=7.1 Hz, 1H), 7.35 (s, 1H), 7.18 (s, 1H), 6.85 (d, J=8.4 Hz, 1H), 5.08 (s, 2H), 4.60 (s, 2H), 2.37 (s, 3H).

Example 11

Preparation of 3-(5-trifluoromethylbenzothiazol-2-yl)methyl-indole-N-acetic Acid 3-(5-trifluoromethylbenzothiazol-2-yl)methyl-indole-N-acetic Acid was prepared in a manner analogous to that set forth in Example 3 (steps 5-7), except 2-amino-4-(trifluoromethyl)-benzenethiol hydrochloride was used instead of 2-amino-3,4,6-trifluorothiophenol hydrochloride in step 6: mp 233-234° C.; $^1$H NMR (DMSO-$d_6$, 300 MHz) δ 8.29 (s, 1H), 8.19 (br d, J=8.1 Hz, 1H), 7.68 (br d, J=9.0 Hz, 1H), 7.49 (br d, J=6.9 Hz, 1H), 7.41 (s, 1H), 7.38 (br d, J=8.4 Hz, 1H), 7.12 (br t, J=6.9 Hz, 1H), 7.00 (br t, J=6.9 Hz, 1H), 5.01 (s, 2H), 4.60 (s, 2H).

Example 12

Preparation of 5-Methyl-3-(5-Trifluoromethylbenzothiazol-2-yl)methyl-indole-N-acetic acid 5-Methyl-3-(5-trifluoromethylbenzothiazol-2-yl)methyl-indole-N-acetic acid was prepared in a manner analogous to that set forth in Example 2, except 5-methylindole was used instead of 5-chloroindole in step 1 and, 2-amino-4-(trifluoromethyl)-benzenethiol hydrochloride was used instead of 2-amino-3,4,6-trifluorothiophenol hydrochloride in step 2 (Example 3, step 6): mp 248-249° C.; $^1$H NMR (DMSO-$d_6$, 300 MHz) δ 8.27 (s, 1H), 8.20 (d, J=8.4 Hz, 1H), 7.68 (d, J=8.4 Hz, 1H), 7.35 (s, 1H), 7.27 (s, 1H), 7.25 (d, J=8.1 Hz, 1H), 6.95 (d, J=8.1 Hz, 1H), 4.96 (s, 2H), 4.57 (s, 2H), 2.31, (s, 3H); LRMS calcd for $C_{20}H_{15}F_3N_2O_2S$. found 405 (M+H).

Example 13

Preparation of 3-(3-nitrophenyl)methyl-indole-N-acetic acid

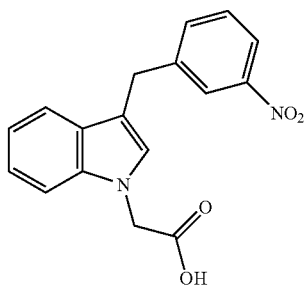

Preparation of Indole-N-Acetic Acid, Ethyl Ester

Under an atmosphere of nitrogen, a solution of indole (15.0 g, 128 mmol) in dry acetonitrile (300 mL, 0.4 M) was treated with sodium hydride (95%, 3.69 g, 153 mmol) and stirred for 30 min. Ethyl bromoacetate (17.0 mL, 153 mmol) was added in a dropwise manner over 10 min and the solution was stirred at room temperature for 16 h. After concentrating under reduced pressure, the resulting residue was dissolved in ethyl acetate and washed with sat'd. aq. NaCl. The organic extracts were dried over MgSO$_4$, filtered and concentrated. The crude product was purified by flash column chromatography (50% ethyl acetate in heptane): Rf0.25 (40% ethyl acetate in heptane) $^1$H NMR (DMSO-$d_6$, 300 MHz) δ 7.53 (d, J=6.3 Hz, 1H), 7.38-7.31 (m, 2H), 7.11 (br t, J=7.2 Hz, 1H), 7.02 (br t, J=7.2 Hz, 1H), 6.45-6.43 (m, 1H), 5.10 (s, 2H), 4.12 (q, J=7.2 Hz, 2H), 1.19 (t, J=7.2 Hz, 3H).

Preparation of 3-(3-nitrophenyl)methyl-indole-N-acetic acid, ethyl ester

Indole-N-acetic acid, ethyl ester (0.500 g, 2.50 mmol) was dissolved in 1,4-dioxane (5 mL) at room temperature with stirring. To this solution was added Ag$_2$CO$_3$/Celite (50% by weight, 0.500 g, 0.9 mmol). The mixture was warmed to 90° C. and maintained overnight. H$_2$O was added to the reaction mixture followed by extracted with EtOAc (2×). The organics were combined and washed with a sat'd brine solution, dried over MgSO$_4$, filtered and concentrated in vacuo. The residue was purified by SiO$_2$ flash chromatography (3:2 Heptane: EtOAc) to give 180 mg (22%) as a pale yellow oil. $^1$H NMR (DMSO-$d_6$, 300 MHz) δ 8.10 (s, 1H), 8.02 (d, J=8.1 Hz, 1H), 7.75 (d, J=7.2 Hz, 1H), 7.59-7.57 (m, 1H), 7.46-7.39 (m, 1H), 7.33 (d, J=8.1 Hz, 1H), 7.20 (s, 1H), 7.13-6.89 (m, 2H), 5.06 (s, 2H), 4.19 (s, 2H), 4.13 (q, J=7.2 Hz, 2H), 1.18 (t, J=7.2 Hz, 3H).

Preparation of 3-(3-nitrophenyl)methyl-indole-N-acetic Acid 3-(3-Nitrophenyl)methyl-indole-N-acetic Acid, ethyl ester (0.175 g, 0.5 mmol) was dissolved in THF:EtOH (1:4, 5 mL) at room temperature with stirring. The mixture was cooled to 0° C. and treated with 1N NaOH (1.55 mL, 1.6 mmol). The mixture was allowed to stir at this temperature for 2 h. 1 N HCl was added and the mixture extracted with EtOAc (2×). The organics were combined and washed with a sat'd brine solution, dried over MgSO$_4$, filtered and concentrated in vacuo. The residue was triturated with heptane and vacuum-filtered with several heptane washings to give 110 mg (69%) the desired compound as an off-white powder. mp 163-165° C.; $^1$H NMR (DMSO-$d_6$, 300 MHz) δ 8.11 (s, 1H), 8.03 (d, J=8.1 Hz, 1H), 7.75 (d, J=8.1 Hz, 1H), 7.53 (t, J=8.1 Hz, 1H), 7.45 (d, J=8.1 Hz, 1H), 7.33 (d, J=8.4 Hz, 1H), 7.20 (s, 1H), 7.11 (t, J=7.2 Hz, 1H), 6.97 (t, J=7.2 Hz, 1H), 4.96 (s, 2H), 4.18 (s, 2H); LRMS calcd for $C_{17}H_{14}N_2O_4S$: 310.0. found 311 (M+1)$^+$.

Example 14

Preparation of 2-phenyl-3-(4,5,7-trifluorobenzothiazol-2-yl)methyl-indole-N-acetic acid

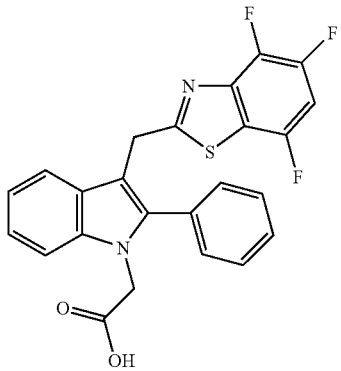

2-phenyl-3-(4,5,7-trifluorobenzothiazol-2-yl)methyl-indole-N-acetic acid was prepared in a manner analogous to that set forth in Example 2, except that 2-phenylindole was used instead of 5-chloroindole in step 1: mp 238-239° C.; R$_f$ 0.60 (10% methanol in chloroform); $^1$H NMR (DMSO-$d_6$, 300 MHz) δ 7.60-7.70 (m, 1H), 7.39-7.58 (m, 7H), 7.20 (t, J=9 Hz, 1H), 7.07 (t, J=9 Hz, 1H), 4.80 (s, 2H), 4.45 (s, 2H); LRMS calcd for $C_{24}H_5F_3N_2O_2S$: 452.0. found 453.0 (M+1)$^+$. Anal. Calcd for $C_{24}H_{15}F_3N_2O_2S$: C, 63.71; H, 3.34; N, 6.19; S, 7.09. Found: C, 63.46; H, 3.32; N, 6.11; S, 6.96.

Example 15

Preparation of 5-phenyl-3-(4,5,7-trifluorobenzothiazol-2-yl)methyl-indole-N-acetic acid 3-cyanomethyl-5-phenyl-indole-N-acetic acid, ethyl ester 5-Bromo-3-cyanomethyl-indole-N-acetic acid, ethyl ester (1.0 g, 3.1 mmol) and phenylboronic acid (0.418 g, 3.4 mmol) were dissolved in anhydrous DME at room temperature under a nitrogen atmosphere and treated with Pd(OAc)$_2$ (2.1 mg, 0.0093 mmol) and PPh$_3$ (7.4 mg, 0.028 mmol). This mixture was heated to reflux and 2 M Na$_2$CO$_3$ (3.11 mL, 6.2 mmol) was added via syringe. After 12 h, the mixture was cooled to room temperature and added to H$_2$O (50 mL). The resultant mixture was extracted with EtOAc (2×, 100 mL) and the organics were combined and washed with a sat'd aqueous NaCl solution, dried over MgSO$_4$, filtered and concentrated in vacuo. The residue was purified by SiO$_2$ flash chromatography (heptane to 1:1 heptane/EtOAc) to give the desired material as a white solid (445 mg, 45%); $^1$H NMR (DMSO-d$_6$, 300 MHz) δ 7.64-7.74 (m, 4H), 7.39-7.44 (m, 4H), 7.29-7.34 (m, 1H), 5.20 (s, 2H), 4.15 (q, J=7.2 Hz, 2H), 4.08 (s, 2H), 1.20 (t, J=7.2 Hz, 3H).

5-phenyl-3-(4,5,7-trifluorobenzothiazol-2-yl)methyl indole-N-acetic acid 5-phenyl-3-(4,5,7-trifluorobenzothiazol-2-yl)methyl-indole-N-acetic acid was prepared in a manner analogous to that set forth in Example 2, except that 5-phenylindole was used instead of 5-chloroindole in step 1: mp 156-159° C.; R$_f$ 0.55 (10% methanol in chloroform); $^1$H NMR (DMSO-d$_6$, 300 MHz) δ 7.66-7.69 (m, 4H), 7.57-7.60 (m, 1H), 7.39-7.47 (m, 3H), 7.29-7.35 (m, 2H), 5.06 (s, 2H), 4.66 (s, 2H); LRMS calcd for C$_{24}$H$_{15}$F$_3$N$_2$O$_2$S: 452.0. found 453.0 (M+1)$^+$. Anal. Calcd for C$_{24}$H$_{15}$F$_3$N$_2$O$_2$S: C, 63.71; H, 3.34; N, 6.19; S, 7.09. Found: C, 63.54; H, 3.32; N, 6.13; S, 7.01.

Example 16

Preparation of 6-phenyl-3-(4,5,7-trifluorobenzothiazol-2-yl)methyl-indole-N-acetic acid Step 1: 6-Phenylindole A solution of 6-bromoindole (2.0 g, 10.20 mmol) in anhydrous toluene (20 mL) under a nitrogen atmosphere was treated with Pd[P(Ph$_3$)]$_4$ (10% mol). After stirring the mixture for 30 min., phenylboronic acid (1.87 g, 15.30 mmol) in anhydrous EtOH (10 mL) was added followed by the addition of sat'd NaHCO$_3$ (6 mL). The bi-phasic mixture was heated to reflux for 24 h. After cooling to room temperature, the mixture was added to a sat'd brine solution and extracted with EtOAc (2×). The organic layer was dried over MgSO4, filtered and concentrated in vacuo. The residue was purified by flash column chromatography (1:1 CH$_2$Cl$_2$/heptane) to give the desired material as white powder (900 mg, 45%): $^1$H NMR (DMSO-d$_6$, 300 MHz) δ 11.15 (br s, 1H), 7.58-7.66 (m, 4H), 7.41-7.47 (m, 2H), 7.36 (m, 1H), 7.26-7.31 (m, 2H), 6.42 (m, 1H).

Preparation of 6-phenyl-3-(4,5,7-trifluorobenzothiazol-2-yl)methyl indole-N-acetic acid 6-phenyl-3-(4,5,7-trifluorobenzothiazol-2-yl)methyl-indole-N-acetic acid was prepared in a manner analogous to that set forth in Example 2, except that 6-phenylindole was used instead of 5-chloroindole in step 1: mp 156-159° C.; R$_f$ 0.50 (10% methanol in chloroform); $^1$H NMR (DMSO-d$_6$, 300 MHz) δ 7.65-7.75 (m, 4H), 7.57-7.62 (m, 1H), 7.41-7.50 (m, 3H), 7.26-7.38 (m, 2H), 5.12 (s, 2H), 4.68 (s, 2H); LRMS calcd for C$_{24}$H$_{15}$F$_3$N$_2$O$_2$S: 452.0. found 453.0 (M+1)$^+$. Anal. Calcd for C$_{24}$H$_{15}$F$_3$N$_2$O$_2$S: C, 63.71; H, 3.34; N, 6.19; S, 7.09. Found: C, 63.46; H, 3.33; N, 6.10; S, 6.96.

Example 17

Preparation of 5-morpholino-3-(4,5,7-trifluorobenzothiazol-2-yl)methyl-indole-N-acetic acid

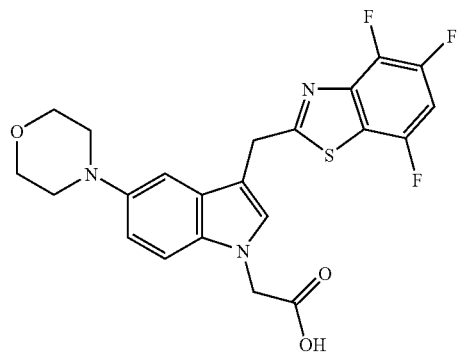

5-Morpholino-2-nitrotoluene

A mixture of 5-fluoro-2-nitrotoluene (5.11 g, 32.9 mmol), morpholine (4.31 mL, 49.4 mmol) and K$_2$CO$_3$ (6.83 g, 49.4 mmol) was diluted in anhydrous DMSO (80 mL) at room temperature with stirring. The mixture was heated to 80° C. for 24 h. After cooling to room temperature, H$_2$O was added and the resultant mixture was extracted with EtOAc (3×, 50 mL). The organic layer was washed with sat'd aqueous NaCl (100 mL), dried over MgSO$_4$, filtered and concentrated in vacuo. The remaining solid was triturated in heptane (200 mL) and filtered to give the desired material (7.10 g, 97%) as a yellow powder: R$_f$ 0.40 (75% heptane/25% ethyl acetate). $^1$H NMR (DMSO-d$_6$, 300 MHz) δ 7.96 (d, J=9.9 Hz, 1H), 8.85-8.88 (m, 2H), 3.70 (t, J=5.0 Hz, 4H), 3.35 (t, J=5.0 Hz, 4H), 2.53 (s, 3H).

Preparation of 5-Morpholinoindole

Under an atmosphere of nitrogen, a solution of 5-morpholinyl-2-nitrotoluene (7.0 g, 31.5 mmol) in DMF (100 mL) was treated with dimethylformamide dimethyl acetal (4.81 mL, 36.2 mmol) and pyrrolidine (2.62 mL, 31.5 mL). The mixture was heated to 100° C. and maintained for 12 h. After cooling, the mixture was concentrated in vacuo to give the desired intermediate as a brick-red solid.

The intermediate enamine was dissolved in EtOAc (200 mL) and added to a pre-charged Parr bottle with 10% Pd/C (600 mg) in EtOAc (40 mL). The mixture was hydrogenated on a Parr-shaker at 55 psi for 2.5 h. The catalyst was filtered through a Celite plug with several washings with EtOAc and the remaining filtrate concentrated in vacuo. The residue was purified by SiO$_2$ flash chromatography (1:1 Hept/EtOAc) to give 2.0 g (31% over 2 steps) of the desired indole as a cream powder: R$_f$ 0.30 (10% methanol in chloroform); $^1$H NMR (DMSO-d$_6$, 300 MHz) δ 10.77 (br s, 1H), 7.24 (s, 1H), 7.18-7.20 (m, 1H), 6.97 (d, J=1.8 Hz, 1H), 6.81 (dd, J$_1$=8.7 Hz, J$_2$=2.1 Hz, 1H), 6.25 (dd, J$_1$=3.0 Hz, J$_2$=1.8 Hz, 1H), 3.7 (t, J=4.50 Hz, 4H), 2.96 (t, J=4.50 Hz, 4H).

Preparation of 5-morpholino-3(4,5,7-trifluorobenzothiazol-2-yl)methyl indole-N-acetic acid 5-morpholino-3-(4,5,7-trifluorobenzothiazol-2-yl) methyl indole-N-acetic acid was prepared in a manner analogous to that set forth in Example 2, except that 5-morpholinoindole was used instead of 5-chloroindole. $^1$H NMR (DMSO-d$_6$, 300 MHz) δ 7.64-7.72 (m, 1H), 7.34 (s, 1H), 7.26 (d, J=9.0 Hz, 1H), 7.06 (d, J=2.4 Hz, 1H), 6.91 (dd, J$_1$=9.0 Hz, J$_2$=2.4 Hz, 1H), 4.95 (s, 2H), 4.60 (s, 2H), 3.70-3.73 (m, 4H), 2.97-3.00 (m, 4H); LRMS calcd for C$_{22}$H$_{18}$F$_3$N$_3$O$_3$S: 461.0. found 462 (M+1)$^+$. Anal. Calcd for C$_{22}$H$_{18}$F$_3$N$_3$O$_3$S.1H$_2$O: C, 55.11; H, 4.20; N, 8.76; S, 6.69. Found: C, 55.11; H, 4.05; N, 8.57; S, 6.50.

Example 18

Preparation of 6-morpholino-3-(4,5,7-trifluorobenzothiazol-2-yl) methyl-indole-N-acetic acid Preparation of 4-Morpholino-2-nitrotoluene A mixture of 4-fluoro-2-nitrotoluene (15.34 g, 98.9 mmol), morpholine (12.94 mL, 49.4 mmol) and K$_2$CO$_3$ (6.83 g, 148.3 mmol) were diluted in anhydrous DMSO (250 mL) at room temperature with stirring. The mixture was heated to 120° C. for 24 h. After cooling to room temperature, H$_2$O was added and the resultant mixture was extracted with EtOAc (3×, 75 mL). The organic layer was washed with sat'd brine (100 mL), dried over MgSO$_4$, filtered and concentrated in vacuo. The remaining solid was triturated in heptane (200 mL) and filtered to give the desired material (8.00 g, 36.4%) as a yellow powder: R$_f$ 0.40 (25% ethyl acetate in heptane). $^1$H NMR (DMSO-d$_6$, 300 MHz) δ 7.40 (d, J=2.7 Hz, 1H), 7.30 (d, J=8.7 Hz, 1H), 7.20 (dd, J$_1$=8.7 Hz, J$_2$=2.7 Hz, 1H), 3.70 (t, J=4.8 Hz, 4H), 3.35 (t, J=4.8 Hz, 4H), 2.36 (s, 3H).

Preparation of 6-Morpholinoindole

Under an atmosphere of nitrogen, a solution of 4-morpholino-2-nitrotoluene (7.1 g, 31.9 mmol) in DMF (100 mL) was treated with dimethylformamide dimethyl acetal (4.92 mL, 37.1 mmol) and pyrrolidine (2.67 mL, 31.9 mL). The mixture was heated to 100° C. and maintained for 12 h. After cooling, the mixture was concentrated in vacuo to give the desired intermediate as a brick-red solid. The crude intermediate was dissolved in glacial HOAc (250 mL) and warmed to 85° C. Zn (18.17 g, 0.278 mol) was added to the solution portionwise over 30 min. The mixture was heated for 4 h. After cooling to room temperature, the mixture was neutralized with sat'd NaHCO$_3$ and extracted with Et$_2$O (3×, 300 mL). The combined organics were washed with sat'd brine, dried over MgSO$_4$, filtered and concentrated in vacuo. The residue was purified by SiO$_2$ flash chromatography (heptane to 2:1 heptane/EtOAc) to give the desired material as a white crystalline powder (1.0 g, 11% over 2 steps): R$_f$ 0.50 (2:1 Heptane/EtOAc); $^1$H NMR (DMSO)-d$_6$, 300 MHz) δ 10.73 (br s, 1H), 7.35 (d, J=8.4 Hz, 1H), 7.11 (d, J=2.4 Hz, 1H), 6.80 (s, 1H), 6.73 (dd, J$_1$=8.4 Hz, J$_2$=2.4 Hz, 1H), 6.25 (d, J=2.4 Hz, 1H), 3.72 (t, J=4.8 Hz, 4H), 3.02 (t, J=4.8 Hz, 1H).

Preparation of 6-morpholino-3-(4,5,7-trifluorobenzothiazol-2-yl)methyl indole-N-acetic acid 6-morpholino-3-(4,5,7-trifluorobenzothiazol-2-yl) methyl indole-N-acetic acid was prepared in a manner analogous to that set forth in Example 2, except that 6-morpholinoindole was used instead of 5-chloroindole in step 1: mp 178-180° C.; $^1$H NMR (DMSO-d$_6$, 300 MHz) δ 7.66-7.72 (m, 1H), 7.37 (d, J=8.4 Hz, 1H), 7.29 (s, 1H), 7.06 (d, J=2.4 Hz, 1H), 6.84 (d, J=8.4 Hz, 1H), 4.96 (s, 2H), 4.58 (s, 2H), 3.37-3.75 (m, 4H), 3.09-3.13 (m, 4H); LRMS calcd for C$_{22}$H$_{18}$F$_3$N$_3$O$_3$S: 461.0. found 462 (M+1)$^+$. Anal. Calcd for C$_{22}$H$_{18}$F$_3$N$_3$O$_3$S CH$_2$Cl$_2$ 0.50H$_2$O: C, 49.74; H, 3.72; N, 7.57; S, 5.77. Found C, 49.73; H, 3.36; N, 7.69; S, 5.58

Example 19

Preparation of 5-phenoxy-3-(4,5,7-trifluorobenzothiazol-2-yl)methyl-indole-N-acetic acid

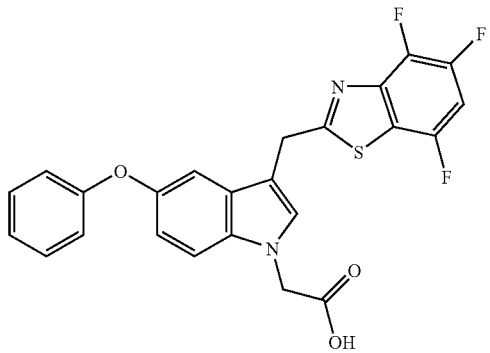

5-Phenoxy-2-nitrotoluene

A solution of phenol (12.16 g, 0.129 mol) in anhydrous DMSO was treated with K$_2$CO$_3$ (17.88 g, 0.129 mol) and stirred at room temperature for 15 min. 5-Fluoro-2-nitrotoluene (13.38 g, 0.086 mol) was added to the solution via syringe. The resultant mixture was heated to 80° C. for 12 h. After cooling to room temperature, the mixture was poured into H$_2$O (100 mL). After extraction with EtOAc (2×, 100 mL), the organics were combined and washed with a sat'd brine solution, drieds over MgSO$_4$, filtered and concentrated in vacuo. The residue was purified by flash column chromatography (heptane to 8:1 heptane/EtOAc) to give the desired material as a yellow crystalline solid (12.50 g, 63%): R$_f$ 0.60 (85% heptane/15% EtOAc); $^1$H NMR (DMSO-d$_6$, 300 MHz) δ 8.05 (d, J=9.0 Hz, 1H), 7.44-7.47 (m, 2H), 7.23-7.29 (m, 1H), 7.12-7.16 (m, 2H), 7.04 (d, J=2.7 Hz, 1H), 6.90 (dd, J$_1$=9.0 Hz, J$_2$=2.7 Hz, 1H), 2.51 (s, 3H).

5-Phenoxyindole

A solution of 5-phenoxy-2-nitrotoluene (10.03 g, 0.0428 mol) in anhydrous DMF was treated with N,N-dimethylformamide dimethyl diacetal (6.73 mL, 0.0508 mol) and pyrrolidine (3.63 mL, 0.0438 mol) and heated to 110° C. for 2.5 h. After cooling to room temperature, the mixture was diluted with EtOAc (500 mL) and washed H$_2$O (500 mL). The organics were dried over MgSO4, filtered and concentrated in vacuo. The crude intermediate was dissolved in glacial HOAc (250 mL) and warmed to 85° C. Zn (24.62 g, 0.377 mol) was added to the solution portion wise over 30 min. The mixture was heated for 4 h. After cooling to room temperature, the mixture was neutralized with sat'd NaHCO$_3$ and extracted with Et$_2$O (3×, 300 mL). The combined organics were washed with sat'd brine, dried over MgSO$_4$, filtered and concentrated in vacuo. The residue was purified by SiO$_2$ flash chromatography (heptane to 2:1 heptane/EtOAc) to give the desired material as a white crystalline powder (3.1 g, 34% over 2 steps): R$_f$ 0.50 (2:1 Heptane/EtOAc); $^1$H NMR (DMSO-d$_6$, 300 MHz) δ 11.12 (br s, 1H), 7.48 (s, 1H), 7.30-7.38 (m, 1H), 7.25-7.29 (m, 2H), 7.17 (d, J=2.7 Hz, 1H), 6.89-7.02 (m, 1H), 6.86-6.88 (m, 2H), 6.80 (dd, J$_1$=8.7 Hz, J$_2$=2.4 Hz, 1H), 6.37 (m, 1H).

Preparation of 5-phenoxy-3-(4,5,7-trifluorobenzothiazol-2-yl)methyl indole-N-acetic acid 5-phenoxy-3-(4,5,7-trifluorobenzothiazol-2-yl) methyl indole-N-acetic acid was prepared in a manner analogous to that set forth in Example 2, except that 5-phenoxyindole was used instead of 5-chloroindole in step 1: mp 128-130° C.; R$_f$ 0.45 (10% methanol in chloroform); $^1$H NMR (DMSO-d$_6$, 300 MHz) δ 7.65-7.70 (m, 1H), 7.47 (s, 1H), 7.42 (d, J=8.4 Hz, 1H), 7.21-7.27 (m, 3H), 6.98 (m, 1H), 6.83-6.90 (m, 3H), 5.02 (s, 2H), 4.60 (s, 2H); LRMS calcd for C$_{24}$H$_{15}$F$_3$N$_2$O$_3$S: 468.0. found 467.0 (M−1)$^-$. Anal. Calcd for C$_{24}$H$_{15}$F$_3$N$_2$O$_3$S: C, 55.11; H, 4.20; N, 8.76; S, 6.69. Found: C, 55.11; H, 4.05; N, 8.57; S, 6.50.

Example 20

Preparation of 7-fluoro-3-(4,5,7-trifluorobenzothiazol-2-yl)methyl-indole-N-acetic acid 7-Fluoro-3-(4,5,7-trifluorobenzothiazol-2-yl)methyl indole-N—acetic acid was prepared in a manner analogous to that set forth in Example 2, except that 7-fluoroindole was used instead of 5-chloroindole in step 1: mp 194-196° C.; R$_f$ 0.60 (10% methanol in chloroform); $^1$H NMR (DMSO-d$_6$, 300 MHz) δ 7.67-7.73 (m, 1H), 7.46 (s, 1H), 7.35 (d, J=7.2 Hz, 1H), 6.89-6.99 (m, 2H), 5.06 (s, 2H), 4.64 (s, 2H); LRMS calcd for C$_{18}$H$_{10}$F$_4$N$_2$O$_2$S.H$_2$O: C, 50.23; H, 3.28; N, 6.51; S, 7.45. Found C, 50.70; H, 2.52; N, 6.60; S, 7.57; 394.0. found 395.0 (M+1)$^+$. Anal. Calcd for C$_{18}$H$_{10}$F$_4$N$_2$O$_2$S

Example 21

Preparation of 7-bromo-3-(4,5,7-trifluorobenzothiazol-2-yl)methyl-indole-N-acetic acid 7-bromo-3-(4,5,7-trifluorobenzothiazol-2-yl)methyl indole-N—acetic acid was prepared in a manner analogous to that set forth in Example 2, except that 7-bromoindole was used instead of 5-chloroindole in step 1: mp 228-230° C.; R$_f$ 0.40 (10% methanol in chloroform); $^1$H NMR (DMSO-d$_6$, 300 MHz) δ 7.65-7.74 (m, 1H), 7.57 (d, J=7.8 Hz, 1H), 7.49 (s, 1H), 7.32 (d, J=7.8 Hz, 1H), 6.94 (t, J=7.8 Hz, 1H), 5.29 (s, 2H), 4.65 (s, 2H); LRMS calcd for C$_{18}$H$_{10}$F$_3$N$_2$O$_2$SBr: 454.0 for ($^{79}$Br and 456.0 for $^{81}$Br). found 453.0 (M−1)$^-$ and 455.0 (M−1)$^-$. Anal Calcd for C$_{18}$H$_{10}$F$_3$N$_2$O$_2$SBr: C, 47.49; H, 2.21; N, 6.15; S, 7.04. Found: C, 47.65; H, 2.27; N, 6.15; S, 6.98.

Example 22

Preparation of 7-chloro-3-(4,5,7-trifluorobenzothiazol-2-yl)methyl-indole-N-acetic acid 7-chloro-3-(4,5,7-trifluorobenzothiazol-2-yl)methyl indole-N—acetic acid was prepared in a manner analogous to that set forth in Example 2, except that 7-chloroindole was used instead of 5-chloroindole in step 1: mp 228-230° C.; R$_f$ 0.38 (10% methanol in chloroform); $^1$H NMR (DMSO-d$_6$, 300 MHz) δ 7.62-7.73 (m, 1H), 7.52 (d, J=7.5 Hz, 1H), 7.49 (s, 1H), 7.15 (d, J=7.5 Hz, 1H), 7.00 (t, J=7.5 Hz, 1H), 5.25 (s, 2H), 4.65 (s, 2H); LRMS calcd for C$_{18}$H$_{10}$F$_3$N$_2$O$_2$SCl: 410.0. found 409.0 (M−1)$^-$. Anal. Calcd for C$_{18}$H$_{10}$F$_3$N$_2$O$_2$SCl: C, 52.63; H, 2.45; N, 6.82; S, 7.81. Found: C, 52.60; H, 2.54; N, 6.66; S, 7.59.

Example 23

3-[5-Fluorbenzothiazole-2-yl]methyl-indole-N-acetic Acid

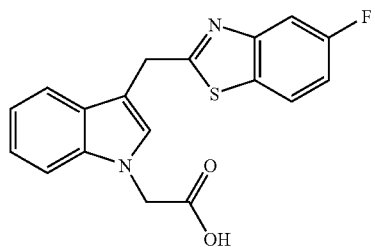

3-[5-fluorbenzothiazole-2-yl]methyl-indole-N-acetic acid was prepared in a manner analogous to that set forth in Example 3, except 2-amino-4-fluorothiophenol hydrochloride was used instead of 2-amino-4,5,7-trifluorothiophenol hydrochloride in step 6: mp 208° C. (decomp); R$_f$ 0.10 (10% methanol in dichloromethane)$^1$H NMR (DMSO-d$_6$, 300 MHz) δ 12.91 (s, 1H), 7.98 (dd, J=8.9, 5.6 Hz: 1H), 7.78 (dd, J=10.0, 2.6 Hz, 1H), 7.50 (d, J=7.8 Hz, 1H), 7.40 (s, 1H), 7.37 (d, J=7.8 Hz, 1H), 7.26 (dt, J=8.9, 2.4 Hz, 1H), 7.13 (t, J=7.8 Hz, 1H), 7.01 (t, J=7.8 Hz, 1H), 5.01 (s, 2H), 4.56 (s, 2H); LRMS m/z 341.0 (M+1)$^+$, 339.0 (M−1). Anal. Calcd for C$_{18}$H$_{13}$FN$_2$O$_2$S: C, 63.52; H, 3.85; N, 8.23; S, 9.42. Found: C, 63.40; H, 3.80; N, 8.37; S, 9.43.

Example 24

3-[6-Fluorbenzothiazole-2-yl]methyl-indole-N-acetic Acid

3-[6-fluorbenzothiazole-2-yl]methyl-indole-N-acetic acid was prepared in a manner analogous to that set forth in Example 3, except 2-amino-5-fluorothiophenol hydrochloride was used instead of 2-amino-4,5,7-trifluorothiophenol hydrochloride in step 6: mp 203° C. (decomp) R$_f$ 0.13 (10% methanol in dichloromethane); $^1$H NMR (DMSO-d$_6$, 300 MHz) δ 12.91 (s, 1H), 7.95 (dd, J=8.9, 5.0 Hz: 1H), 7.86 (dd, J=8.8, 2.8 Hz, 1H), 7.50 (d, J=7.5 Hz, 1H), 7.40-7.35 (m, 2H), 7.32 (dt, J=8.9, 2.7 Hz, 1H), 7.13 (t, J=7.6 Hz, 1H), 7.00 (t, J=7.6 Hz, 1H), 5.01 (s, 2H), 4.54 (s, H); LRMS m/z 341.0 (M+1)$^+$, 339.0 (M−1. Anal. Calcd for C$_{18}$H$_{13}$FN$_2$O$_2$S: C, 63.52; H, 3.85; N, 8.23; S, 9.42. Found: C, 63.52; H, 3.86; N, 8.35; S, 9.53.

The compounds of Examples 25-32 were prepared essentially according to the procedures set forth above in examples 1 and/or 2 with appropriate substitution of starting materials.

Example 25

3-(4,5,7-trifluorobenzothiazol-2-yl)methyl-indole-N-2-propionic acid

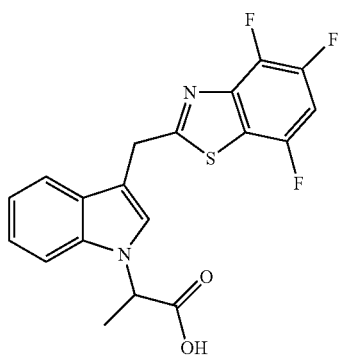

mp 176-177° C.; $R_f$ 0.34 (20% methanol in dichlormethane); $^1$H NMR (DMSO-$d_6$, 300 MHz) δ 7.60-7.73 (m, 1H), 7.60 (s, 1H), 7.52 (d, J=8.1 Hz, 1H), 7.44 (d, J=8.1 Hz, 1H), t, J=7.5 Hz, 1H), 7.02 (t, J=7.5 Hz, 1H), 5.35 (q, J=8.1 Hz, 1H), 4.64 (s, 2H), 1.72 (d, J=8.1 Hz, 3H); LRMS calcd for $C_{19}H_{13}F_3N_2O_2S$: 390.0. Found 391.0 (M+1)$^+$. Anal. Calcd for $C_{19}H_{13}F_3N_2O_2S$·$H_2O$: C, 55.88; H, 3.70; N, 6.86; S, 7.85. Found: C, 56.09; H, 3.31; N, 6.89; S, 7.99.

Example 26

3-(4-5,7-trifluorobenzothiazol-2-yl)methyl-indole-N-3-propionic acid

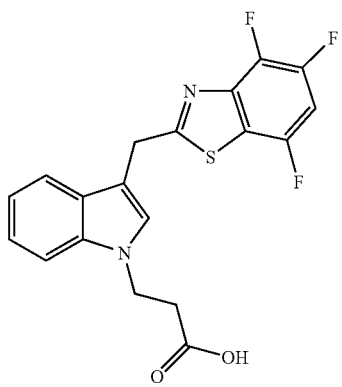

mp 200-201° C.; $R_f$ 0.50 (20% methanol in dichloromethane); $^1$H NMR (DMSO-$d_6$, 300 MHz) δ 7.63-7.71 (m, 1H), 7.51 (s, 1H), 7.47 (d, J=3.0 Hz, 2H), 7.14 (t, J=7.5 Hz, 1H), 7.00 (t, J=7.5 Hz, 1H), 4.61 (s, 2H), 4.39 (t, J=6.6 Hz, 2H), 2.75 (t, J=6.6 Hz, 2H); LRMS calcd for $C_{19}H_{13}F_3N_2O_2S$: 390.0. Found 391.0 (M+1)$^+$. Anal Calcd for $C_{19}H_{13}F_3N_2O_2S$: C, 58.46; H, 3.36; N, 7.18; S, 8.21. Found: C, 58.63; H, 3.40; N, 7.20; S, 8.30.

Example 27

Preparation of 6-Bromo-3-(5-trifluoromethylbenzothiazol-2-yl)methyl-indole-N-acetic acid: mp 265-267° C.; $R_f$ 0.19 (20% methanol in dichloromethane); $^1$H NMR (DMSO-$d_6$, 300 MHz) δ 8.28 (s, 1H), 8.22 (d, J=8.7 Hz, 1H), 7.67-7.69 (m, 2H), 7.43-7.47 (m, 2H), 7.14 (d, J=9.0 Hz, 1H), 5.04 (s, 2H), 4.61 (s, 2H); LRMS calcd for $C_{19}H_{12}F_3N_2O_2SBr$: 469.0. Found 469.0 (M+1)$^+$ for Br=79. Anal. Calcd for $C_{19}H_{12}F_3N_2O_2SBr$: C, 48.63; H, 2.58; N, 5.97; S, 6.83. Found: C, 48.60; H, 2.63; N, 5.88; S, 6.91.

Example 28

6-Methoxy-3-(4,5,7-trifluorobenzothiazol-2-yl)methyl-indole-N-acetic acid: mp 118-120° C.; $R_f$ 0.27 (20% methanol in dichloromethane); $^1$H NMR (DMSO-$d_6$, 300 MHz) δ 7.63-7.73 (m, 1H), 7.39 (s, 1H), 7.28 (d, J=8.7 Hz, 1H), 7.07 (s, 1H), 6.78 (d, J=8.7 Hz, 1H), 4.97 (s, 2H), 4.61 (s, 2H); 3.07 (s, 3H); LRMS calcd for $C_{19}H_{13}F_3N_2O_3S$: 406.0. Found 407.0 (M+)$^+$. Anal. Calcd for $C_{19}H_{13}F_3N_2O_3S$·$H_2O$: C, 53.77; H, 3.56; N, 6.60; S, 7.56 Found: C, 53.87; H, 3.56; N, 6.67; S, 7.67.

Example 29

4-Chloro-3-(4,5,7-trifluorobenzothiazol-2-yl)methyl-indole-N-acetic acid

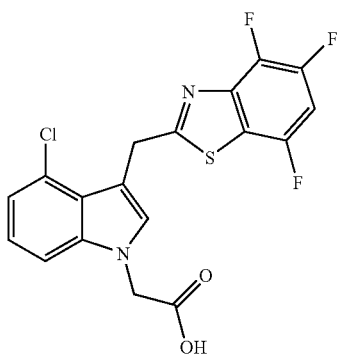

mp 203-206° C.; $R_f$ 0.24 (20% methanol in dichloromethane); $^1$H NMR (DMSO-$d_6$, 300 MHz) δ 7.63-7.71 (m, 1H), 7.57 (s, 1H), 7.33 (d, J=9.0 Hz, 1H), 7.12 (dd, J(1)=9.0, J(2)=7.8 Hz, 1H), 7.03 (d, J=7.8 Hz, 1H), 5.08 (s, 2H), 4.78 (s, 2H); LRMS calcd for $C_{18}H_{10}F_3N_2O_2SCl$: 410.0. Found 411.0 (M+1)$^+$ and 409.0 (M−1)$^-$.

Example 30

5-Methoxy-3-(4,5,7-trifluorobenzothiazol-2-yl)methyl-indole-N-acetic acid

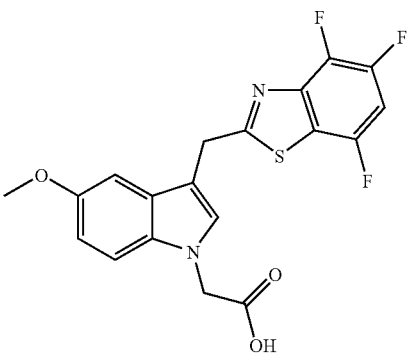

mp 165-167° C.; $R_f$ 0.37 (20% methanol in dichloromethane); $^1$H NMR (DMSO-$d_6$, 300 MHz) δ 7.61-7.70 (m, 1H), 7.35 (d, J=9.0 Hz, 1H), 7.26 (s, 1H), 6.90 (s, 1H), 6.64 (d, J=9.0 Hz, 1H), 4.79 (s, 2H); 4.56 (s, 2H), 3.72 (s, 3H); LRMS calcd for $C_{10}H_{13}F_3N_2O_2S$: 406.0. Found 407.0 (M+1)$^+$ and 405.0 (M−1)$^−$.

Example 31

5-Bromo-3-(4,5,7-trifluorobenzothiazol-2-yl) methyl-indole-N-acetic acid: mp 209-294° C.; $R_f$ 0.18 (20% methanol in dichloromethane); $^1$H NMR (DMSO-$d_6$, 300 MHz) δ 7.78 (d, J=1.8 Hz, 1H), 7.65-7.73 (m, 1H), 7.49 (s, 1H), 7.61 (d, J=9.0 Hz, 1H), 7.25 (dd, J(1)=9.0 Hz, J(2)=1.8 Hz, 1H), 5.04 (s, 2H); 4.64 (s, 2H); LRMS calcd for $C_{18}H_{10}F_3N_2O_2SBr$: 455.0. Found 455.0 (M+1)$^+$ for Br 79 and 457 (M+1)$^+$ for Br 81.

Example 32

3-(6-chlorobenzothiazol-2-yl) methyl-indole-N-acetic acid

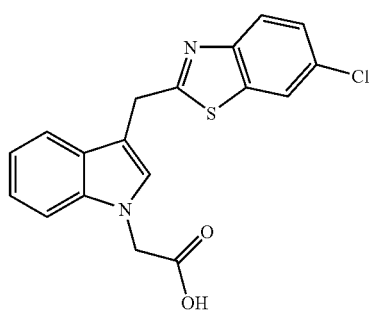

Representative compounds of the invention were tested for their potency, selectivity and efficacy as inhibitors of human aldose reductase. The potency or aldose reductase inhibiting effects of the compounds were tested using methods similar to those described by Butera et al. in *J. Med. Chem.* 1989, 32, 757. Using this assay, the concentrations required to inhibit human aldose reductase (hALR2) activity by 50% (IC50) were determined.

In a second assay, a number of the same compounds were tested for their ability to inhibit aldehyde reductase (hALR1), a structurally related enzyme. The test method employed were essentially those described by Ishii, et al., *J. Med. Chem.* 1996 39: 1924. Using this assay, the concentrations required to inhibit human aldehyde reductase activity by 50% (IC50) were determined.

From these data, the hALR1/hALR2 ratios were determined. Since high potency of test compounds as inhibitors of aldose reductase is desirable, low hALR2 IC50 values are sought. On the other hand, high potency of test compounds as inhibitors of aldehyde reductase is undesirable, and high hALR1 IC50s values are sought. Accordingly, the hALR1/hALR2 ratio is used to determine the selectivity of the test compounds. The importance of this selectivity is described in Kotani, et al., *J. Med. Chem.* 40: 684, 1997.

The results of all these tests are combined and illustrated in Table 1.

| Example # | hALR2 (IC50) | HALR1 (IC50) | HALR1/hALR2 |
|---|---|---|---|
| 1 | 8 nM | 13,000 nM | 1,200 |
| 2 | 10 nM | 11,000 nM | 1,100 |
| 3 | 5 nM | 27,000 nM | 5,400 |
| 4 | 8 nM | 34,000 nM | 4,250 |
| 5 | 6 nM | 21,000 nM | 3,500 |
| 6 | 8 nM | 2,700 nM | 340 |
| 7 | 12 nM | 4,800 nM | 400 |
| 8 | 7 nM | 7,500 nM | 1,100 |
| 9 | 11 nM | 21,000 nM | 1,900 |
| 10 | 5 nM | 13,000 nM | 2,600 |
| 11 | 99 nM | 5,600 nM | 57 |
| 12 | 102 nM | 10,000 nM | 98 |
| 13 | 73 nM | 13,000 nM | 178 |
| 14 | 101 nM | 16,000 | 160 |
| 15 | 53 nM | 10,000 | 190 |
| 16 | 25 nM | 6,200 nM | 248 |
| 17 | 8 nM | 41,000 nM | 5,100 |
| 18 | 15 nM | >100 μM | >6,700 |
| 19 | 30 nM | 11,000 nM | 370 |
| 20 | 7 nM | 7,000 nM | 1,000 |
| 21 | 14 nM | 18,000 nM | 1,300 |
| 22 | 9.1 nM | 19,000 nM | 2,100 |
| 23 | 9 nM | 6,500 nM | 720 |
| 24 | 1,040 nM | 4,500 nM | 4 |
| 25 | 160 nM | 6,500 nM | 41 |
| 26 | 17 nM | 88,000 nM | 5,200 |
| 27 | 52 nM | <5,000 nM | <96 |
| 28 | 5 nM | 12,000 nM | 2,400 |
| 29 | 11 nM | 14,000 | 1,270 |
| 30 | 7.7 nM | 21,000 nM | 2,700 |
| 31 | 13 nM | 9,700 | 746 |
| 32 | 660 nM | Not Tested | Not Tested |
| Tolrestat | 13 nM | 1,940 nM | 149 |

The results show the superior potency, selectivity and efficacy of representative compounds of the invention. Such compounds are useful in the treatment of chronic complications arising from diabetes mellitus, such as diabetic cataracts, retinopathy and neuropathy. Accordingly, an aspect of the invention is treatment of such complications with the inventive compounds; treatment includes both prevention and alleviation. The compounds are useful in the treatment of, for example, diabetic cataracts, retinopathy, nephropathy and neuropathy.

In a third, optional, set of experiments, the compounds can be assayed for their ability to normalize or reduce sorbitol accumulation in the sciatic nerve of streptozotocin-induced diabetic rats. The test methods employed to determine the efficacy are essentially those of Mylari, et al., *J. Med. Chem.* 34: 108, 1991.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

We claim:
1. A compound of the formula:

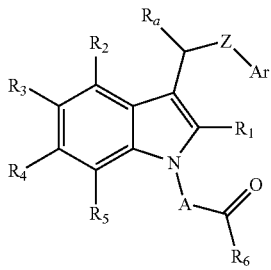

wherein

A is a $C_1$-$C_4$ alkylene group optionally substituted with $C_1$-$C_2$ alkyl or mono- or disubstituted with halogen;

Z is a bond, O, S, C(O)NH, or $C_1$-$C_3$ alkylene optionally substituted with $C_1$-$C_2$ alkyl;

$R_1$ is hydrogen, alkyl having 1-6 carbon atoms, halogen, 2-, 3-, or 4-pyridyl, or phenyl, where the phenyl or pyridyl is optionally substituted with up to three groups selected from halogen, hydroxy, $C_1$-$C_6$ alkoxy, $C_1$-$C_6$ alkyl, nitro, amino, or mono- or di($C_1$-$C_6$)alkylamino;

$R_2$, $R_3$, $R_4$ and $R_5$ are each independently
hydrogen, halogen, nitro, or an alkyl group of 1-6 carbon atoms optionally substituted with one or more halogens;
$OR_7$, $SR_7$, $S(O)R_7$, $S(O)_2N(R_7)_2$, $C(O)N(R_7)_2$, or $N(R_7)_2$, wherein each $R_7$ is independently hydrogen, an alkyl group of 1-6 carbon atoms optionally substituted with one or more halogens, or benzyl, where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino;
phenyl or heteroaryl, where each of which phenyl or heteroaryl is optionally substituted with up to three groups independently selected from halogen, $C_1$-$C_6$ alkyl, $C_1$-$C_6$ alkoxy, amino, and mono- or di($C_1$-$C_6$) alkylamino;
phenoxy where the phenyl portion is optionally substituted with up to three groups independently selected from halogen, $C_1$-$C_6$ alkyl, $C_1$-$C_6$ alkoxy, amino, and mono- or di($C_1$-$C_6$)alkylamino; or
a group of the formula

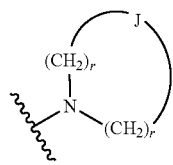

where
J is a bond, $CH_2$, oxygen, or nitrogen; and
each r is independently 2 or 3;

$R_6$ is hydroxy, benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-ylmethyl, $C_1$-$C_6$ alkoxy or $O^-M^+$ where $M^+$ represents a cation selected from sodium, potassium, ammonium, magnesium and calcium;

$R_a$ is hydrogen, $C_1$-$C_6$ alkyl, fluoro, or trifluoromethyl;

and Ar represents a heteroaryl group selected from
a heterocyclic 5-membered ring having one nitrogen, oxygen or sulfur, two nitrogens one of which may be replaced by oxygen or sulfur, or three nitrogens one of which may be replaced by oxygen or sulfur, said heterocyclic 5-membered ring being condensed with benzo, said benzo being optionally substituted by one of iodo, cyano, nitro, perfluoroethyl, trifluoroacetyl, or ($C_1$-$C_6$) alkanoyl, one or two of fluoro, chloro, bromo, hydroxy, ($C_1$-$C_6$)alkyl, ($C_1$-$C_6$)alkoxy, ($C_1$-$C_6$)alkylthio, trifluoromethoxy, trifluoromethylthio, ($C_1$-$C_6$)alkylsulfinyl, ($C_1$-$C_6$)alkylsulfonyl or trifluoromethyl, or two fluoro or two trifluoromethyl with one hydroxy or one ($C_1$-$C_6$) alkoxy, or one or two fluoro and one trifluoromethyl, or three fluoro;

a heterocyclic 6-membered ring having one to three nitrogen atoms, or one or two nitrogen atoms and one oxygen or sulfur, said heterocyclic 6-membered ring being condensed with benzo, where the benzo is optionally substituted by one of iodo or trifluoromethylthio, or one or two of fluoro, chloro, bromo, ($C_1$-$C_6$)alkyl, ($C_1$-$C_6$) alkoxy, ($C_1$-$C_6$)alkylthio, ($C_1$-$C_6$)alkylsulfinyl, ($C_1$-$C_6$) alkylsulfonyl, or trifluoromethyl;

said benzo-condensed heterocyclic 5-membered or 6-membered rings being optionally substituted in the heterocyclic 5-membered or 6-membered ring by one of fluoro, chloro, bromo, methoxy, or trifluoromethyl; and the benzo-condensed heterocyclic 5-membered ring and the benzo-condensed heterocyclic 6-membered ring are connected to Z via a ring member of the heterocyclic 5-membered or 6-membered ring, respectively.

2. A compound according to claim 1, wherein Ar is a heteroaryl group which is a heterocyclic 5- or 6-membered ring fused to a benzo group of Formula III

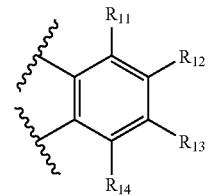

wherein $R_{11}$, $R_{12}$, $R_{13}$ and $R_{14}$ are independently hydrogen, fluorine, chlorine, bromine, trifluoromethyl or nitro.

3. A compound according to claim 2, wherein A is methylene and Z is a bond.

4. A compound according to claim 2, wherein $R_a$ is hydrogen and Z is a bond.

5. A compound according to claim 2, wherein A is methylene, $R_a$ is hydrogen, and Z is a bond.

6. A compound according to claim 1, wherein the heterocyclic 5- or 6-membered ring fused to a benzo group is optionally substituted on the benzo portion by one of iodo, cyano, nitro, perfluoroethyl, trifluoroacetyl, or ($C_1$-$C_6$)alkanoyl, one or two of fluoro, chloro, bromo, hydroxy, ($C_1$-$C_6$)alkyl, ($C_1$-$C_6$)alkoxy, ($C_1$-$C_6$) alkylthio, trifluoromethoxy, trifluoromethylthio, ($C_1$-$C_6$)alkyl-sulfinyl, ($C_1$-$C_6$)alkylsulfonyl or trifluoromethyl, or two fluoro or two trifluoromethyl with one hydroxy or one ($C_1$-$C_6$)alkoxy, or one or two fluoro and one trifluoromethyl, or three fluoro.

7. A compound according to claim 6, wherein at least one of $R_{11}$, $R_{12}$, $R_{13}$, and $R_{14}$ is trifluoromethyl.

8. A compound according to claim 7, wherein $R_{12}$ is trifluoromethyl.

9. A compound according to claim 6, wherein $R_{11}$, $R_{12}$, and $R_{14}$ are fluorines and $R_{13}$ is hydrogen.

10. A compound according to claim 9, wherein $R_6$ is hydroxy.

11. A compound according to claim 9, wherein $R_6$ is $C_1$-$C_6$alkoxy.

12. A compound according to claim 5, wherein $R_{13}$ is hydrogen.

13. A compound according to claim 12, wherein $R_6$ is hydroxy.

14. A compound according to claim 12, wherein $R_6$ is $C_1$-$C_6$ alkoxy.

15. A pharmaceutical composition comprising an effective amount of a compound according to claim 1 and a pharmaceutically acceptable carrier.

16. A compound according to claim 2, wherein Ar is a heterocyclic 6-membered ring containing one nitrogen and the ring is fused to a benzo group of Formula III

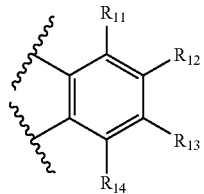

III wherein $R_{11}$, $R_{12}$, $R_{13}$ and $R_{14}$ are independently hydrogen, fluorine, chlorine, bromine, trifluoromethyl or nitro.

17. A method of alleviating chronic complications arising from diabetes mellitus, which comprises administering to a mammal in need of such treatment an effective amount of a compound according to claim 1 wherein the complications are selected from the group consisting of diabetic cataracts, retinopathy, nephropathy and neuropathy.

* * * * *